US010881700B1

(12) United States Patent
Hajjar et al.

(10) Patent No.: US 10,881,700 B1
(45) Date of Patent: Jan. 5, 2021

(54) COMPOSITIONS INCLUDING EXTRACTS OF GRAY MANGROVE LEAVES AND METHODS OF TREATMENT USING SUCH COMPOSITIONS IN TREATMENT OF VIRAL INFECTIONS

(71) Applicant: KING ABDULLAH UNIVERSITY OF SCIENCE AND TECHNOLOGY, Thuwal (SA)

(72) Inventors: Dina Ahmed Hajjar, Thuwal (SA); Stephan Kremb, Abu Dhabi (AE); Christian Voolstra, Thuwal (SA); Timothy Ravasi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 33 days.

(21) Appl. No.: 15/725,888

(22) Filed: Oct. 5, 2017

Related U.S. Application Data

(60) Provisional application No. 62/406,563, filed on Oct. 11, 2016.

(51) Int. Cl.
*A61K 36/00* (2006.01)
*A61K 36/19* (2006.01)
*A61K 45/06* (2006.01)

(52) U.S. Cl.
CPC .............. *A61K 36/19* (2013.01); *A61K 45/06* (2013.01); *A61K 2236/333* (2013.01)

(58) Field of Classification Search
None
See application file for complete search history.

(56) References Cited

PUBLICATIONS

Khafagi et al. (2003) Egyptian Journal of Biology, vol. 5, pp. 62-69. (Year: 2003).*
Namazi et al. (2013) Iranian Journal of Pharmaceutical Research, 12(2): 435-443. (Year: 2013).*
Prabhu et al. (2012) Der Pharmacia Sinica 3(1): 64-70. (Year: 2012).*
Zandi et al. (2008) International Journal of Infectious Diseases 12, Supplement 1, e298. (Year: 2008).*
De Bethune MP. Non-nucleoside reverse transcriptase inhibitors (NNRTIs), their discovery, development, and use in the treatment of HIV-1 infection: a review of the last 20 years (1989-2009). Antiviral research, 2010;85(1):75-90.
Kim BS, et al. Identification of a novel type of small molecule inhibitor against HIV-1. BMB reports, 2015;48(2):121.
Deeks SG and AN Phillips. Clinical review: HIV infection, antiretroviral treatment, ageing, and non-AIDS related morbidity. Bmj, 2009;338:288-292.
Kremb S, et al. Aqueous extracts of the marine brown alga Lobophora variegate inhibit HIV-1 infection at the level of virus entry into cells. PloS one, 2014;9(8):e103895.
Jung M, et al. Recent studies on natural products as anti-HIV agents. Current medicinal chemistry, 2000;7(6):649-661.
Lai Mt, et al. In vitro characterization of MK-1439, a novel HIV-1 nonnucleoside reverse transcriptase inhibitor. Antimicrobial agents and chemotherapy, 2014;58(3):1652-1663.
Young DW, et al. Integrating high-content screening and ligand-target prediction to identify mechanism of action. Nature chemical biology, 2008;4(1):59-68.
Schulze CJ, et al. "Function-first" lead discovery: made of action profiling of natural product libraries using image-based screening. Chemistry & biology, 2013;20(2):285-295.
Korn K, Krausz E. Cell-based high-content screening of small-molecule libraries. Current opinion in chemical biology, 2007;11(5):503-510.
Sumiya E, et al. Cell-morphology profiling of a natural product library identifies bisebromoamide and miuraenamide A as actin filament stabilizers. ACS chemical biology, 2011;6(5):425-431.
Shum D, et al. High-content assay to identify inhibitors of dengue virus infection. Assay and drug development technologies, 2010;8(5):553-570.
Giuliano KA, et al. High-content screening: a new approach to easing key bottlenecks in the drug discovery process. Journal of Biomolecular Screening, 1997;2(4):249-259.

(Continued)

*Primary Examiner* — Russell G Fiebig
(74) *Attorney, Agent, or Firm* — Pabst Patent Group LLP

(57) ABSTRACT

Human Immunodeficiency Virus (HIV) causes AIDS, a life-threatening disease characterized by immunosuppressive, opportunistic infections and malignancies. Although many drugs have been approved over the past decade as suitable for use in the treatment of individuals with HIV, the need for antiviral drugs of greater efficiency is still pressing. One valuable source for antiviral bioactivity has been proven to be the natural products of a wide range of plants. In this study, we investigated the anti-reverse transcriptase (RT)-HIV-1 potential activity of *Avicennia marina* (gray mangrove) collected from the Red Sea shore, Saudi Arabia. Metabolites from *A. marina* were extracted using organic solvents followed by solid phase extraction (SPE) and high-performance liquid chromatography (HPLC). Gas chromatography mass spectrometry (GC-MS) was applied to assess the active HPLC fractions and to establish a correlation between the fractions' chemical composition and biological activity. The chemical analyses revealed the existence of many polyphenol compounds. Polyphenol compounds have been proven to act as multi-target anti-HIV agents. Furthermore, imaging-based High-Content Screening (HCS) with a set of cellular staining was established to characterize mechanisms of activity and potential side-effects, such as toxicity and cell cycle arrest. In summary, we discovered and assessed for the first time anti-RT-HIV-1 activity for *A. marina* collected from Red Sea shore, Saudi Arabia. Our results suggest this plant is a promising candidate for the development of potential novel HIV-1 inhibitors.

11 Claims, 11 Drawing Sheets

(56) References Cited

PUBLICATIONS

Voolstra R, S.K.a.C. High-resolution phenotypic profiling of natural products—induced effects on the single-cell level. Submitted, 2016.

Berridge MV, et al. The biochemical and cellular basis of cell proliferation assays that use terazolium salts. Biochemica, 1996;4(1):14-19.

Singh IP, et al. Anti-HIV natural products. Current Science-Bangalore, 2005;89(2):269.

Yang J, et al. A natural theaflavins preparation inhibits HIV-1 infection by targeting the entry step: potential applications for preventing HIV-1 infection. Fitoterapia, 2012;83(2):348-355.

Behbahani M. Evaluation of anti-HIV-1 activity of a new iridoid glycoside isolated from Avicenna marina, in vitro. International immunopharmacology, 2014;23(1):262-266.

Kim HJ, et al. HIV-1 integrase inhibitory phenylpropanoid glycosides from Clerodendron trichotomum. Archives of pharmacal research, 2001;24(4):286-291.

Andrae-Marobela K, et al. Polyphenols: a diverse class of multi-target anti-HIV-1 agents. Current drug metabolism, 2013;14(4):392-413.

Prakash B, et al. Safety assessment of Zanthoxylum alatum Roxb, essential oil, its antifungal, antiaflatoxin, antioxidant activity and efficacy as antimicrobial in preservation of *Piper nigrum* L. fruits. International journal of food microbiology, 2012;153(1):183-191.

Huang QS, et al. Inhibitory effects of methyl trans-cinnamate on mushroom tyrosinase and its antimicrobial activities. Journal of agricultural and food chemistry, 2009;57(6):2565-2569.

Lima FJ, et al. Antispasmodic and myorelaxant effects of the flavoring agent methyl cinnamate in gut: Potential inhibition of tyrosine kinase. European Journal of pharmacology, 2014;740:192-199.

Vasconcelos-Silva AA, et al. Vasorelaxation induced by methyl cinnamate, the major constituent of the essential oil of Ocimum micranthum, in rat isolated aorta. Clinical and Experimental Pharmacology and Physiology, 2014;41(1):755-762.

Mazumder A, et al. Inhibition of human immunodeficiency virus type-1 integrase by curcumin. Biochemical pharmacology, 1995;49(8):1165-1170.

James CA, et al. Nucleotide competing reverse transcriptase inhibitors: Discovery of a series of non-basic benzofurano [3, 2-d] pyrimidin-2-one derived inhibitors. Bioorganic & medicinal chemistry letters, 2013;23 (9):2781-2786.

Murry JP, et al. Sulfonation pathway inhibitors block reactivation of latent HIV-1. Virology, 2014;471:1-12.

Malek SNA, et al. Cytotoxic components of pereskin bleo (kunth) DC (Cactaceae) leaves. Molecules, 2009;14 (5):1713-1724.

Sani HL, et al. Effects of standardized stem bark extract of *Mangifera indica* L in wistar rats with 2, 4-dinitrophenylhydrazine-induced haemolytic anaemia. Pharmacognosy Journal, 2015;7(2):89-96.

Yoon MA, et al. Antioxidant effects of quinolone alkaloids and 2, 4-di-tert-butylphenol isolated from Scolopendra subspinipes. Biological and Pharmaceutical Bulletin, 2006;29(4):735-739.

Dharmi S, et al. Purification, characterization, and in vitro activity of 2, 4-di-tert-butylphenol from Pseudomonas monteilii PsF84: conformational and molecular docking studies. Journal of agricultural and food chemistry, 2014;62 (26):6138-6146.

Gerlier D, Thomasset N. Use of MTT colorimetric assay to measure cell activation. Journal of immunological methods, 1986;94(1-2):57-63.

Van Meerloo J, et al. Cell sensitivity assays: the MTT assay. Cancer cell culture: methods and protocols, 2011;237-245.

Huang C, et al. Polyphenol-rich *Avicennia marina* leaf extracts induce apoptosis in human breast and liver cancer cells and in a nude mouse xenograft model. Oncotarget, 2016.

Behbahani M, Sadeghi-Aliabadi H. Antiproliferative activity and apoptosis induction of crude extract and fractions of avicennia marina. Iranian journal of basic medical sciences, 2013;16(11):1203-1208.

Bhimba BV, et al. Anticancer and antimicrobial activity of mangrove derived fungi *Hypocrea lixii* VB1. Chinese Journal of Natural Medicine, 2012;10(1):0077-0080.

\* cited by examiner

COMPOSITIONS INCLUDING EXTRACTS OF GRAY MANGROVE LEAVES AND METHODS OF TREATMENT USING SUCH COMPOSITIONS IN TREATMENT OF VIRAL INFECTIONS

RELATED APPLICATIONS

This application claims the benefit of priority of United States provisional application number U.S. 62/406,563, filed Oct. 11, 2016, the entire contents of which application is incorporated by reference here.

FIELD OF THE INVENTION

The presented invention relates to extracts of certain Saudi Arabian medicinal herbs which have been found to be and thus useful in the treatment or inhibition of viral disease states and conditions, particularly HIV disease states and conditions, including AIDS and ARC. Pharmaceutical compositions based upon these extracts represent an additional aspect of the invention. Methods of treating or inhibiting viral disease states and conditions through the application of the extracts represent an additional aspect of the invention.

BACKGROUND OF THE INVENTION

For the first time since the emergence of AIDS almost three decades ago, the survival rate of individuals infected with HIV is on the rise. This is at least true for patients in developed countries [1]. AIDS is caused by the human immunodeficiency virus type 1 (HIV-1). This virus has been isolated and is the target of antiretroviral drugs. Many drugs have been developed, in a relatively short time frame; over 25 approved drugs are available for prescription to patients infected with HIV-1[2, 3]. These drugs are not problem-free, however. They are expensive and viral resistance and severe side effects have been reported. These issues stimulate continued research in this area [4]. The antiretrovira drugs currently on the market often work by attacking viral enzymes, in a variety of ways. For example, reverse transcriptase (RT) inhibitors, which make up the majority of approved drugs [2, 5], act by blocking an important step in HIV-1 replication. RT has polymerase and RNase H activity and is involved in synthesizing double-stranded proviral DNA from single-stranded viral RNA. Inhibiting this process therefore restricts viral replication and has been a popular target when developing antiviral drugs. Patients diagnosed with the HIV-1 infection will generally receive highly active antiretroviral therapy (HAART). This is treatment with 3 or more medications that have different modes of action, thereby providing a broad antiviral coverage. The result of this approach to treatment is often a significant, and ongoing, suppression of the virus. In many cases, the patient's immune system has been allowed to recover and progression to clinical disease has been prevented[6].

Much information on the activity of natural products, using both single molecules and fractionated biological extracts, has been made available through imaging-based High-Content Screening (HCS)[7-9]. This approach provides a wealth of data, of a broader nature than that provided by toxicity testing of cancer cell lines as a measure of anti-neoplastic activity, for example. HCS can be used to study the pathways that lead to toxicity by showing multiple levels of cell physiology [7, 8, 10]. In many studies, HCS was used to accelerate the drug discovery process and development of promising new bioactivities. HCS is primarily applied to study the side-effects of bioactive compounds in vitro, leading to improvements in candidate discovery and clinical trials [11, 12].

BRIEF DESCRIPTION OF THE INVENTION

The present invention recognizes that certain herbs may be effective in treating, inhibiting, preventing, reducing the incidence of, ameliorating or resolving viral disease states or conditions. To address this potential, a known Saudi Arabian herb, *Avicennia marina* (gray mangrove leaves), was examined for effectiveness against HIV. The *A. marina* leaves were collected from the Red Sea shore. High-performance liquid chromatography (HPLC) fractions were acquired from active solid phase extracts that possess activity on anti RT-HIV-1 based on biochemical assay. Chemical profiling of active fractions of *A. marina* was undertaken using GC-MS. Furthermore, automated imaging-based High-Content Screening was used to investigate toxicity and cell cycle effect of *A. marina* compounds and reveal some information about their mechanism of activity and their potential side effect in vitro system.

The present invention relates to extracts obtained from *Avicennia marina* (gray mangrove leaves). Such herbs or chemical constituents thereof are viral inhibitors and accordingly are effective in pharmaceutical compositions or nutritive supplements to treat, inhibit, prevent, reduce the incidence of, ameliorate and/or resolve viral disease states or conditions.

One or more aqueous or alcoholic (e.g. methanolic or ethanolic, preferably methanolic) extracts pursuant to the present invention can be used alone or in combination with a pharmaceutically acceptable carrier, additive or excipient to treat, inhibit, prevent, reduce the incidence of, ameliorate and/or resolve a number of disease states or conditions including, for example, cancer. The herbal compositions of the present invention can be use to treat patients, who have cancer.

The present invention also contemplates a method of treating, inhibiting, preventing, reducing the incidence of, ameliorating or resolving a viral disease state or condition, comprising administering to said patient an effective amount of a composition including an herb (especially including an extract) obtained from *Avicennia marina* (gray mangrove leaves). In preferred embodiments, the virus is selected from HIV I and/or II, and the condition is AIDS or ARC. In a most preferred embodiment, the virus is HIV I and/or II.

BRIEF DESCRIPTION OF THE DRAWINGS

FIG. 1A is a scatter plot showing the results of measuring the HIV-RT activity on the presence of SPE extract. The X-axis shows the extracts designation and on the Y-axis the activity of the HIV-RT. FIG. 1B shows hit extracts as re-tested in serial dilution for the active SPE extracts fractions. The black line shows the cut off to distinguish non-active from active extracts.

FIGS. 1A and 2B are graphs showing an evaluation of the effect of HPLC fraction extract on RT-HIV-1 biochemical assay. FIG. 1A shows the percentage of RT-HIV-1 inhibition using L_C18_40% HPLC fraction treatment on RT-HIV-1 biochemical assay.

FIG. 1B shows L_CN-E_EA % HPLC fraction treatment on RT-HIV-1 biochemical assay.

FIG. 3B is a graph summarizing the data set for cytological profiling of *A. marina* leaves. The complete data set was visualized using multiple experiment viewers (MeV).

FIGS. 3A and 4B are graphs showing the effect of *A. marina* leaves SPE fractions on HeLa cells. FIG. 4B shows the effect of SPE fractions on Cell cycle distribution.

FIG. 5B shows a detail of FIG. 5A on an enlarged scale. FIG. 5C shows a detail of FIG. 5B, on an even larger scale, showing the place of *Avicennia marina* collection. Pictures were generated on Google Earth.

DETAILED DESCRIPTION OF THE INVENTION

Figures 1A, 1B:
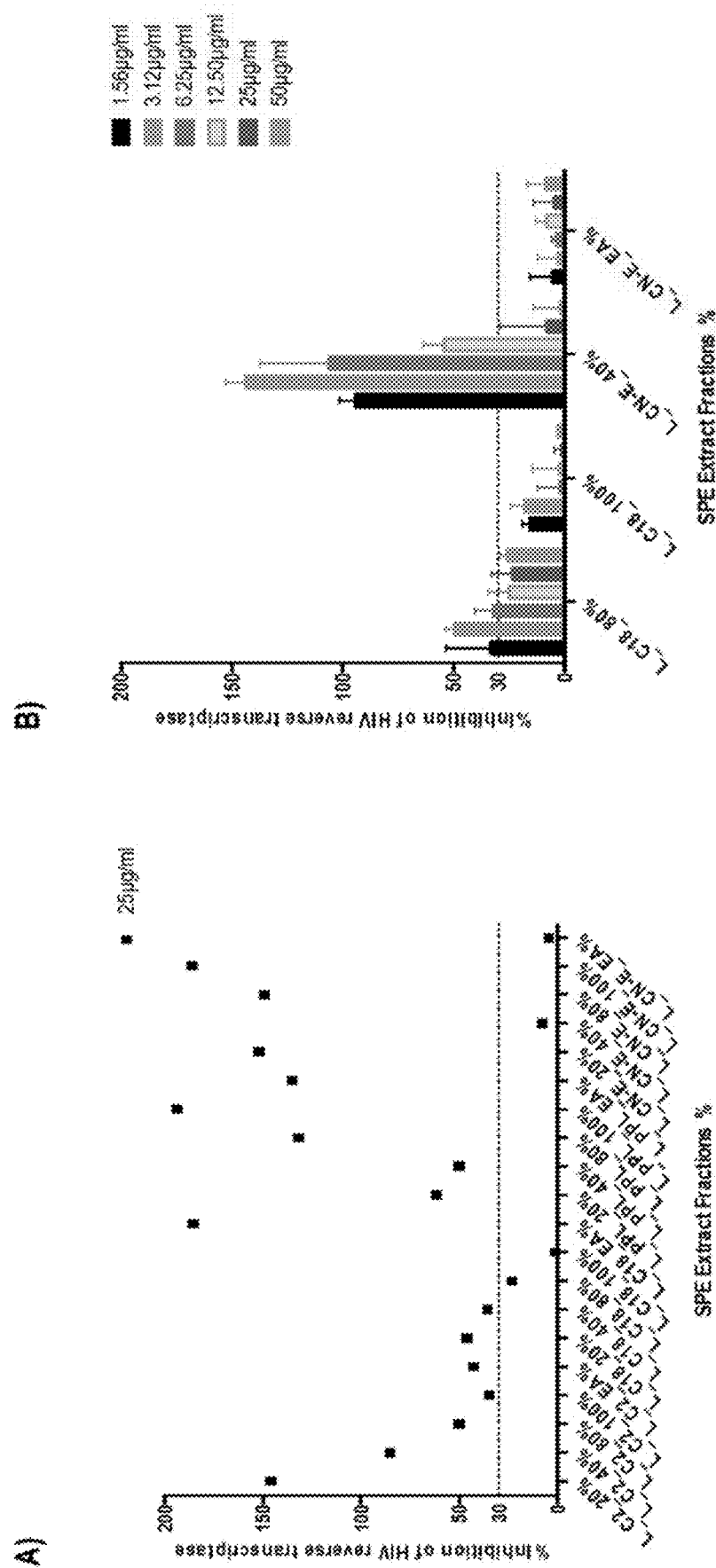
FIGS. 1A and 1B are a pair of graphs illustrating results of a study of the effect of *A. marina* SPE extracts fractions on the activity of HIV-RT.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used. Where a substituent is not disclosed it is presumed (unless contrary to the underlying chemistry) that the substituent is a hydrogen atom.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification to describe an animal, preferably a domesticated animal or a human, more preferably a human to whom treatment, including prophylactic treatment, with the compositions according to the present invention is provided. For treatment of those infections, conditions or disease states which are specific for a specific animal such as a human patient, the term "patient" refers to that specific animal. In general, in the present invention, the term "patient" refers to a human patient unless otherwise stated. In the present invention, in addition to humans, domesticated animals (e.g., horses, cows, dogs, cats, pigs, sheep, goats, etc.) also may be commonly treated.

The term "compound" is used herein to describe any specific chemical compound disclosed herein and includes tautomers, regioisomers, geometric isomers, and where applicable, optical isomers (enantiomers) thereof, as well as pharmaceutically acceptable salts and alternative salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds (at least about 70% enantiomerically enriched, preferably greater than 90% enantiomerically enriched and in certain preferred embodiments, substantially pure or pure enantiomers where the compound is more than 98-99% or more enantiomerically enriched). It is understood by those of ordinary skill that molecules which are described herein are stable compounds as generally described hereunder and variables are chosen (often in combination) which promote the stability of the compound described.

The term "virus" is used herein to describe a virus, such as HIVI or HIVII. In a most preferred embodiment, the virus is HIV I and/or II.

The term "effective" is used to describe an amount of a component, extract, material or solvent which is used to produce an intended effect in amount consistent the effect desired and may vary with the effect desired or which occurs.

The term "extract" is used to describe an extract (an aqueous, $C_1$-$C_3$ alcohol, including methanol and/or ethanol or aqueous alcohol, preferably water or aqueous methanol or ethanol extract) of one or more of the Saudi Arabian herb *Avicennia marina*. In preferred embodiments, the solvent is methanol or aqueous methanol containing less than 5% water.

Extracts of the present invention are prepared by exposing one or more of the herbs which are described above to an effective amount of an aqueous or alcohol solvent (an aqueous, $C_1$-$C_3$ alcohol, including ethanol or aqueous alcohol, preferably water or aqueous ethanol), preferably heated (including boiling) for a period of time effective to extract medicinal components of the herbs into the solvent. Extracts of solvents may be prepared using standard methods readily available in the art and may include the preferred methods of preparation as otherwise described herein.

The term "aqueous" is used to describe a solvent which comprises water in any amount. In certain embodiments, extracts are provided using water or water/alcohol, preferably water/methanol (preferably, including at least about 50% by volume water within this mixture) solvent, preferably solvent, especially including methanol which is heated (preferably boiled).

The term "$C_1$-$C_3$ alcoholic" or "$C_1$-$C_3$ alcoholic solvent" is used to describe a solvent which contains a $C_1$-$C_3$ alcohol in amounts greater than 50% and often greater than 95% (approaching up to 100%) by volume, in certain embodiments in combination with water.

The terms "methanolic", "ethanolic", "methanol solvent" or "ethanolic solvent" are used to describe a solvent which comprises methanol and/or or ethanol in amounts greater than 50% and often greater than 95% (approaching up to 100%) by volume, often in combination with water. As noted, the terms "alcoholic", "methanolic" and/or "ethanolic" may overlap with the term "aqueous" as otherwise defined herein. In preferred aspects of the infection, the solvent is methanol or aqueous methanol with no more than about 5% water.

The term "solid extract" is used to describe an extract of one or more of the herbs as otherwise disclosed herein which has been dried, dehydrated, lyophilized or otherwise solidified to avoid containing appreciable quantities of solvent.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the bifunction ARM-HI compounds described above, are coadministered in combination with at least one additional anti-HIV agent as otherwise described herein in a cocktail for the treatment of HIV infections. In particularly preferred aspects of the invention, the coadministration of compounds results in synergistic anti-HIV activity of the therapy.

The term "additional anti-HIV agent" shall mean a traditional anti-HIV agent (ie., a non-bifunctional ARM-HI compound as otherwise described herein) which may be co-administered to a patient along with ARM-HI compounds according to the present invention in treating a patient for HIV. Such compounds include, for example, agents such as nucleoside reverse transcriptase inhibitors (NRTI), non-nucloeoside reverse transcriptase inhibitors, protease inhibitors and fusion inhibitors. Exemplary compounds include, for example, Amprenivir, Abacavir, Acemannan, Acyclovir, AD-439, AD-519, Adefovir dipivoxil, Alpha Interferon, Ansamycin, 097, AR 177, Beta-luoro-ddA, BMS-232623 (CGP-73547), BMS-234475 (CGP-61755), CI-1012, Cidofovir, Curdlan sulfate, Cytomegalovirus Immune globin, Ganciclovir, Dideoxyinosine, DMP-450, Efavirenz (DMP-266), EL10, Famciclovir, FTC, GS 840, HBY097, Hypericin, Recombinant Human Interferon Beta, Interferon alfa-n3, Indinavir, ISIS-2922, KNI-272, Lamivudine (3TC), Lobucavir, Nelfinavir, Nevirapine, Novapren, Peptide T Octapeptide Sequence, Trisodium Phosphonoformate, PNU-140690, Probucol, RBC-CD4, Ritonavir, Saquinavir, Valaciclovir, Virazole Ribavirin, VX-478, Zalcitabine, Zidovudine (AZT), Tenofovir diisoproxil fumarate salt, Combivir, Abacavir succinate, T-20), AS-101, Bropirimine, CL246, EL10, FP-21399, Gamma Interferon, Granulocyte Macrophage Colony Stimulating Factor (GM-CSF), HIV Core Particle Immunostimulant, Interleukin-2 (IL-2), Immune Globulin Intravenous, IMREG-1, IMREG-2, Imuthiol Diethyl Dithio Carbamate, Alpha-2 Interferon, Methionine-Enkephalin, MTP-PE (Muramyl-Tripeptide), Granulocyte Colony Stimulating Factor (GCSF), Remune, rCD4 (Recombinant Soluble Human CD4-IgG), rCD4-IgG Hybrids, Recombinant Soluble Human CD4, Interferon Alfa 2a, SK&F1-6528, Soluble T4, Thymopentin, Tumor Necrosis Factor (TNF), AK602, Alovudine, Amdoxovir, AMD070, Atazanavir (Reyataz), AVX754 (apricitabine), Bevirimat, BI-201, BMS-378806, BMS-488043, BMS-707035, C31G, Carbopol 974P, Calanolide A, Carrageenan, Cellulose sulfate, Cyanovirin-N, Darunavir, Delavirdine, Didanosine (Videx), Efavirenz, Elvucitabine, Emtricitabine, Fosamprenavir (Lexiva), Fozivudine tidoxil, GS 9137, GSK-873,140 (aplaviroc), GSK-364735, GW640385 (brecanavir), HG0004, HGTV43, INCB9471, KP-1461, Lopinavir, Mifepristone (VGX410), MK-0518, PPL-100, PRO 140, PRO 542, PRO 2000, Racivir, SCH-D (vicriviroc), SP01A, SPL7013, TAK-652, Tipranavir (Aptivus), TNX-355, TMC125 (etravirine), UC-781, UK-427,857 (Maraviroc), Valproic acid, VRX496, Zalcitabine, Valganciclovir, Clindamycin with Primaquine, Fluconazole Pastille, Nystatin Pastille, Eflornithine, Pentamidine, Isethionate, Trimethoprim, Trimethoprim/sulfa, Piritrexim, Pentamidine isethionate, Spiramycin, Intraconazole-R51211, Trimetrexate, Daunorubicin, Recombinant Human Erythropoietin, Recombinant Human Growth Hormone, Megestrol Acetate, Testosterone, Aldesleukin (Proleukin), Amphotericin B, Azithromycin (Zithromax), Calcium hydroxyapatite, Doxorubicin, Dronabinol, Entecavir, Epoetin alfa, Etoposide, Fluconazole, Isoniazid, Itraconazole (Sporanox), Megestrol, Paclitaxel (Taxol), Peginterferon alfa-2, Poly-L-lactic acid (Sculptra), Rifabutin (Mycobutin), Rifampin, Somatropin and Sulfamethoxazole/ Trimethoprim. Preferred anti-HIV compounds for use in the present invention include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof.

The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The present invention relates to herb extract compositions, especially solid extracts or extracts which are based at least in part on aqueous, $C_1$-$C_3$ alcoholic (methanol, ethanol, propanol, isopranol, preferably ethanol), especially water, aqueous alcohol, especially aqueous methanol or ethanolic (preferably, methanolic) solvents of *Avicennia marina*. Further aspects of the invention relate to compositions which comprise an effective amount of an herb extract in liquid, semi-solid or solid form (especially including lyophized), optionally in combination with a pharmaceutically acceptable carrier, additive or excipient. These compositions may be used to prevent, treat, ameliorate, or reduce the incidence of various viral disease states or conditions, comprising administering an effective amount of an extract as otherwise described herein to a patient in need thereof.

Pharmaceutical compositions according to the present invention comprise an effective amount of one or more compounds according to the present invention optionally in combination with a pharmaceutically acceptable additive, carrier or excipient. In particular aspects pharmaceutical compositions comprise a therapeutically effective amount of at least one compound selected from the compounds found in Tables 1, 2 or 3 hereof or a pharmaceutically acceptable salt, stereoisomer, solvate or polymorph thereof. In certain preferred embodiments, the compound is at least one compound selected from the group consisting of 2-methoxyphenol, methyl m-methylbenzoate, methyl cinnamate (or a stereoisomer, including an enantiomer or racemate thereof) and 2,4,-t-butylphenol alone or in combination with one or more other compounds which are set forth in Tables 1, 2 or 3 hereof, or a pharmaceutically acceptable salt, stereoisomer, solvate or polymorph thereof.

In another aspect, the present invention is directed to the use of one or more extracts or pharmaceutical composition hereof according to the present invention in a pharmaceutically acceptable carrier, additive or excipient at a suitable dose ranging from about 0.05 to about 100 mg/kg of body weight per day, preferably within the range of about 0.1 to 50 mg/kg/day, most preferably in the range of 1 to 20 mg/kg/day. The desired dose may conveniently be presented in a single dose or as divided doses administered at appropriate intervals, for example as two, three, four or more sub-doses per day.

Ideally, the active ingredient should be administered to achieve effective peak plasma concentrations of the active compound preferably within the range of from about 0.05 to about 5 uM. This may be achieved, for example, by oral or other route of administration as otherwise described herein. Oral dosages, where applicable, will depend on the bioavailability of the compounds from the GI tract, as well as the pharmacokinetics of the compounds to be administered. While it is possible that, for use in therapy, a compound of the invention may be administered as the raw chemical, it is preferable to present the active ingredient as a pharmaceutical formulation, presented in combination with a pharmaceutically acceptable carrier, excipient or additive.

Pharmaceutical formulations include those suitable for oral, rectal, nasal, topical (including buccal and sub-lingual), vaginal or parenteral (including intramuscular, subcutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution, with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

Formulations containing the compounds of the invention may take the form of solid, semi-solid, lyophilized powder, or liquid dosage forms, such as, for example, tablets, capsules, powders, sustained-release formulations, solutions, suspensions, emulsions, sup-positories, creams, ointments, lotions, aerosols or the like, preferably in unit dosage forms suitable for simple administration of precise dosages.

The compositions typically include a conventional pharmaceutical carrier, additive or excipient and may additionally include other medicinal agents, carriers, and the like. Preferably, the composition will be about 0.05% to about 75-80% by weight of an extract or extracts of the invention, with the remainder consisting of suitable pharmaceutical additives, carriers and/or excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the extracts in liquid, semi-solid or solid form (about 0.5% to about 20%), and optional pharmaceutical additives, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Methods for preparing such dosage forms are known or will be apparent to those skilled in the art; for example, see "Remington's Pharmaceutical Sciences" (17th Ed., Mack Pub. Co, 1985). The person of ordinary skill will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients in the treatment of any one or more of the disease states or conditions which are treated with herbal extracts according to the present invention. Effective amounts or concentrations of each of the active compounds are to be included within the pharmaceutical compositions according to the present invention.

The individual components of such combinations may be administered either sequentially or simultaneously in separate or combined pharmaceutical formulations.

When one or more of the compounds according to the present invention is used in combination with a second therapeutic agent active the dose of each compound may be either the same as or differ from that when the compound is used alone. Appropriate doses will be readily appreciated by those skilled in the art.

In method aspects according to the present invention, one or more pharmaceutical compositions according to the present invention may be administered to a patient in the treatment or prevention of any disease state or condition previously mentioned. An effective amount of an herbal extract as otherwise described herein is administered to a patient exhibiting symptoms of a disease state or condition as otherwise described herein in order to treat the symptoms of the disease states and/or conditions and reduce or eliminate the likelihood that the disease state or condition will deteriorate.

Pharmaceutical compositions according to the present invention comprise an effective amount of one or more of the extracts in liquid, semi-liquid or solid form, otherwise described herein, optionally in combination with a pharmaceutically acceptable carrier, additive or excipient, and further optionally in combination with at least one additional agent useful in treating a disease state or condition which is related to or modulated through NRF2 protein. In this aspect of the invention, multiple compounds may be advantageously formulated to be coadministered for the prophylactic and/or therapeutic treatment of any one or more of the disease states or conditions described hereinabove.

The individual components of such combinations as described above may be administered either sequentially or simultaneously in separate or combined pharmaceutical formulations. When one or more of the extracts according to the present invention is used in combination with a second therapeutic agent active the dose of each may be either the same as or differ from that when the compound is used alone. Appropriate doses will be readily appreciated by those skilled in the art.

The term "coadministration" is used to describe the administration of two or more active compounds, in this case a compound according to the present invention, in combination with an additional anti-viral agent or other biologically active agent, in effective amounts. Although the term coadministration preferably includes the administration of two or more active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

The term "human immunodeficiency virus" shall be used to describe human immunodeficiency virus 1 (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A category 2 (ARC) infection is characterized by the following criteria: The patient's T-cells have dropped below 500 but never below 200, and that patient has never had any Category 3 diseases (as set forth below) but have had at least one of the following defining illnesses:

Bacillary angiomatosis

Candidiasis, oropharyngeal (thrush)

Candidiasis, vulvovaginal; persistent, frequent, or poorly responsive to therapy Cervical dysplasia (moderate or severe)/cervical carcinoma in situ Constitutional symptoms, such as fever (38.5 C) or diarrhea lasting longer than 1 month Hairy leukoplakia, oral Herpes zoster (shingles), involving at least two distinct episodes or more than one dermatome
   Idiopathic thrombocytopenic purpura
   Listeriosis
   Pelvic inflammatory disease, particularly if complicated by tubo-ovarian abscess
   Peripheral neuropathy
According to the U.S. government, in Category 2 ARC, the immune system shows some signs of damage but it isn't life-threatening.
A Category 3 (AIDS) infection is characterized by the following criteria:
   T-cells have dropped below 200 or
   Patent has (has had) at least one of the following defining illnesses—
   Candidiasis of bronchi, trachea, or lungs
   Candidiasis, esophageal
   Cervical cancer, invasive**
   Coccidioidomycosis, disseminated or extrapulmonary
   Cryptococcosis, extrapulmonary
   Cryptosporidiosis, chronic intestinal (greater than 1 month's duration)
   Cytomegalovirus disease (other than liver, spleen, or nodes)
   Cytomegalovirus retinitis (with loss of vision)
   Encephalopathy, HIV-related
   Herpes simplex: chronic ulcer(s) (greater than 1 month's duration); or bronchitis, pneumonitis, or esophagitis
   Histoplasmosis, disseminated or extrapulmonary
   Isosporiasis, chronic intestinal (greater than 1 month's duration)
   Kaposi's sarcoma
   Lymphoma, Burkitts (or equivalent term)
   Lymphoma, immunoblastic (or equivalent term)
   Lymphoma, primary, of brain
   *Mycobacterium avium* complex or *M. kansasii*, disseminated or extrapulmonary
   *Mycobacterium tuberculosis*, any site (pulmonary** or extrapulmonary)
   *Mycobacterium*, other species or unidentified species, disseminated or extrapulmonary
   *Pneumocystis carinii* pneumonia
   Pneumonia, recurrent**
   Progressive multifocal leukoencephalopathy
   *Salmonella* septicemia, recurrent
   Toxoplasmosis of brain
   Wasting syndrome due to HIV
   Additional anti-HIV agents which are useful in the treatment of HIV (other than extracts of the present invention) or a secondary condition thereof, include, for example, nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), Festinavir, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.
   Other agents which may be used in coadministration with compounds according to the present invention include, for example, other NNRTI's (i.e., other than the NNRTI's according to the present invention) may be selected from the group consisting of nevirapine, delavirdine, efavirenz, UC-781(N-[4-chloro-3-(3-methyl-2-butenyloxy)phenyl]-2methyl-3-furancarbothiamide), etravirine, Trovirdine, MKC-442 (emivirine, coactinon), HI-236, HI-240, HI-280, HI-281, rilpivirine, MSC-127, HBY 097, DMP266, Baicalin (TJN-151), Methyl 3-Bromo-5-(1-5-bromo-4-methoxy-3-(methoxycarbonyl)phenyl)hept-1-enyl)-2-methoxybenzoate, 5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl) suifone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscamet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyraziny)-3H-1,2-dithiole-3-thione), N-{2-(2-Chloro-6-fluorophenethyl]-N'-(2-thiazolyl)thiourea), N-{2-(2,6-Difluorophenethyl]-N'-[2-(5-bromopyridyl)]thiourea, N-{2-(2,6-Difluorophenethyl]-N'-[2-(5-methylpyridyl)]thiourea, N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl]-5-ethyl-6-methyl (pypridin-2(1H)-thione, 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoinidol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.
   In the present study, we investigated the anti-viral potential activity of *A. marina* leaves collected from the Red Sea shore. High-performance liquid chromatography (HPLC) fractions were acquired from active solid phase extracts that possess activity on anti RT-HIV-1 based on biochemical assay. Chemical profiling of active fractions of *A. marina* was preformed using GC-MS that provide deep insight about the chemical compounds. Furthermore, we used automated imaging-based High-Content Screening to investigate toxicity and cell cycle effect of *A. marina* compounds and reveal some information about their mechanism of activity and their potential side effect in vitro system.
Materials and Methods
   Sample Collection and Identification
   Sample Collection and Identification.

Figures 5A, 5B, 5C:
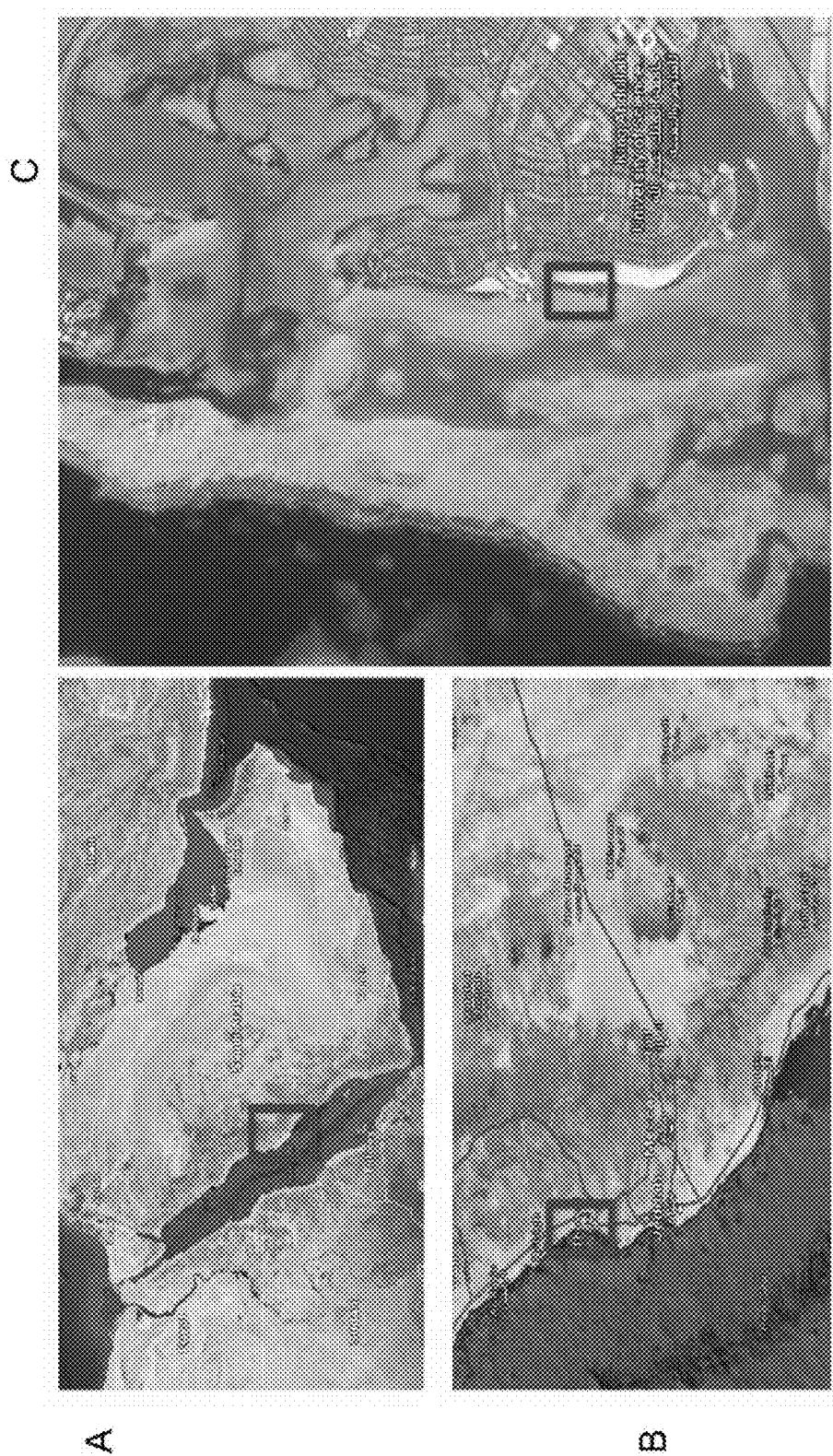
FIGS. 5A-5C are satellite maps of increasing scale of Saudia Arabia and the northern Red Sea coast.
Figure 6:
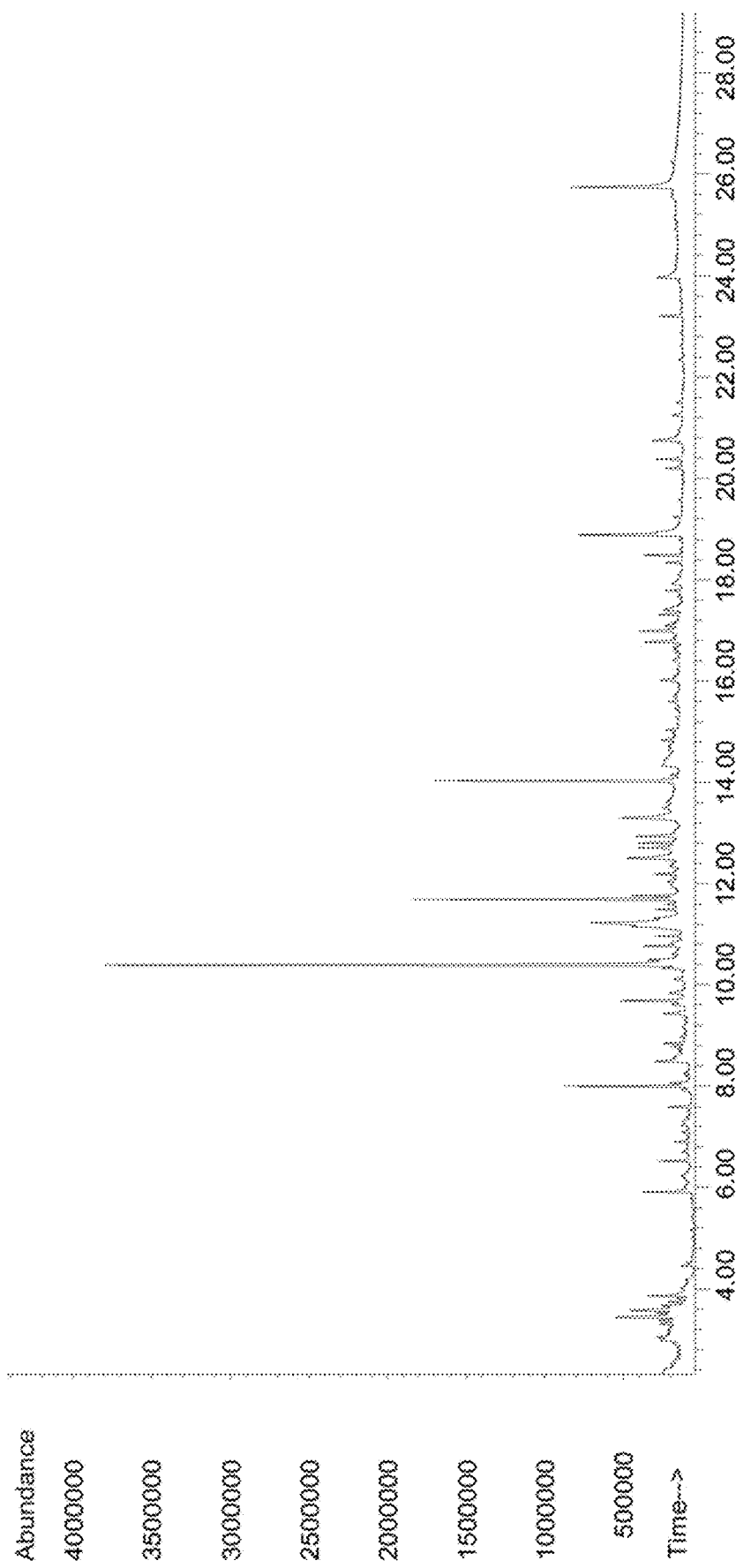
FIG. 6 is a GC/MS chromatogram of plant extract Fraction #3 from L_C18_40% HPLC fractions.
Figures 7A, 7B, 7C:
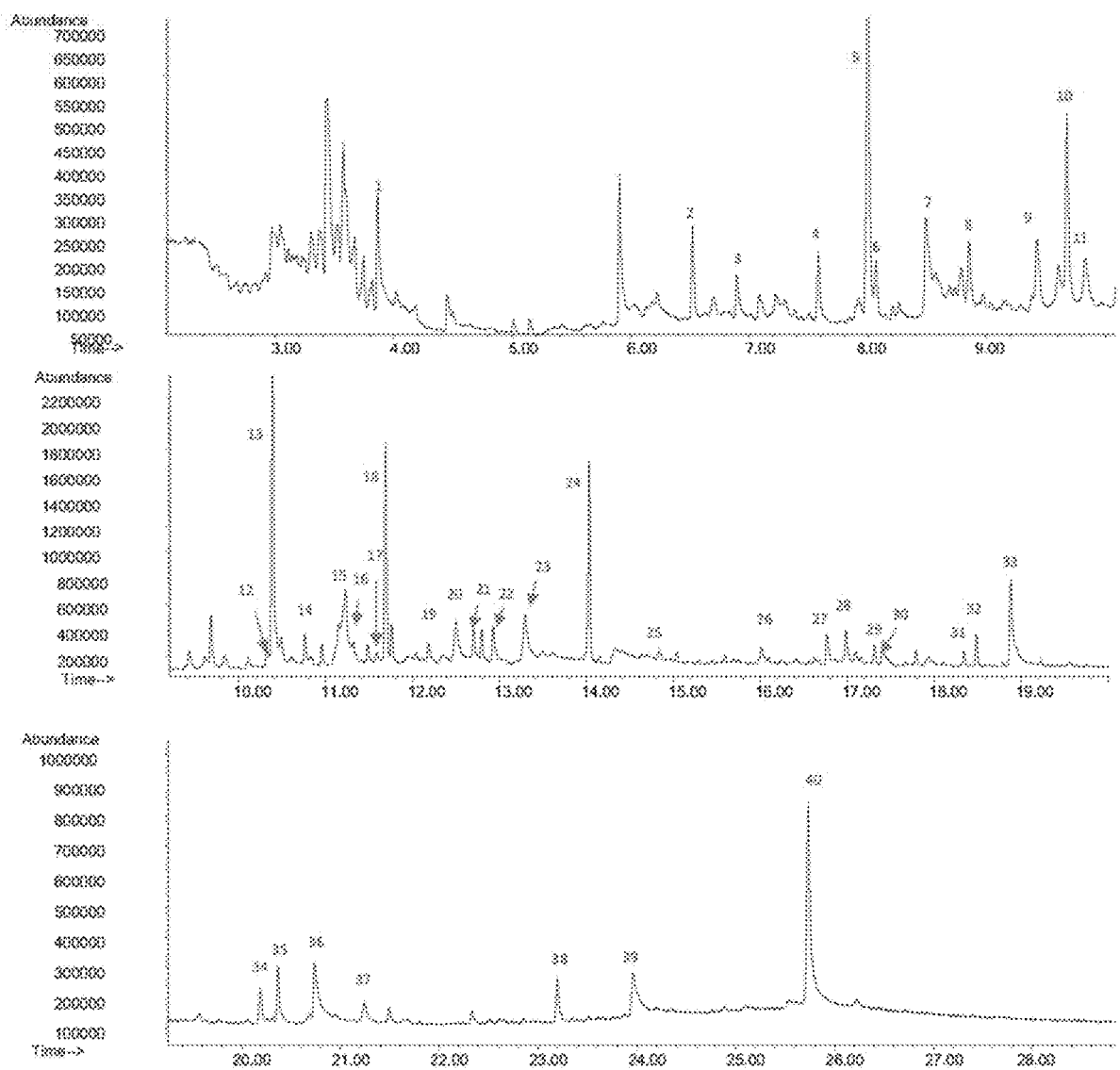
FIGS. 7A-7C are three graphs showing respective regions of the GC/MS chromatogram of FIG. 6, on an enlarged time scale.
Figure 8:
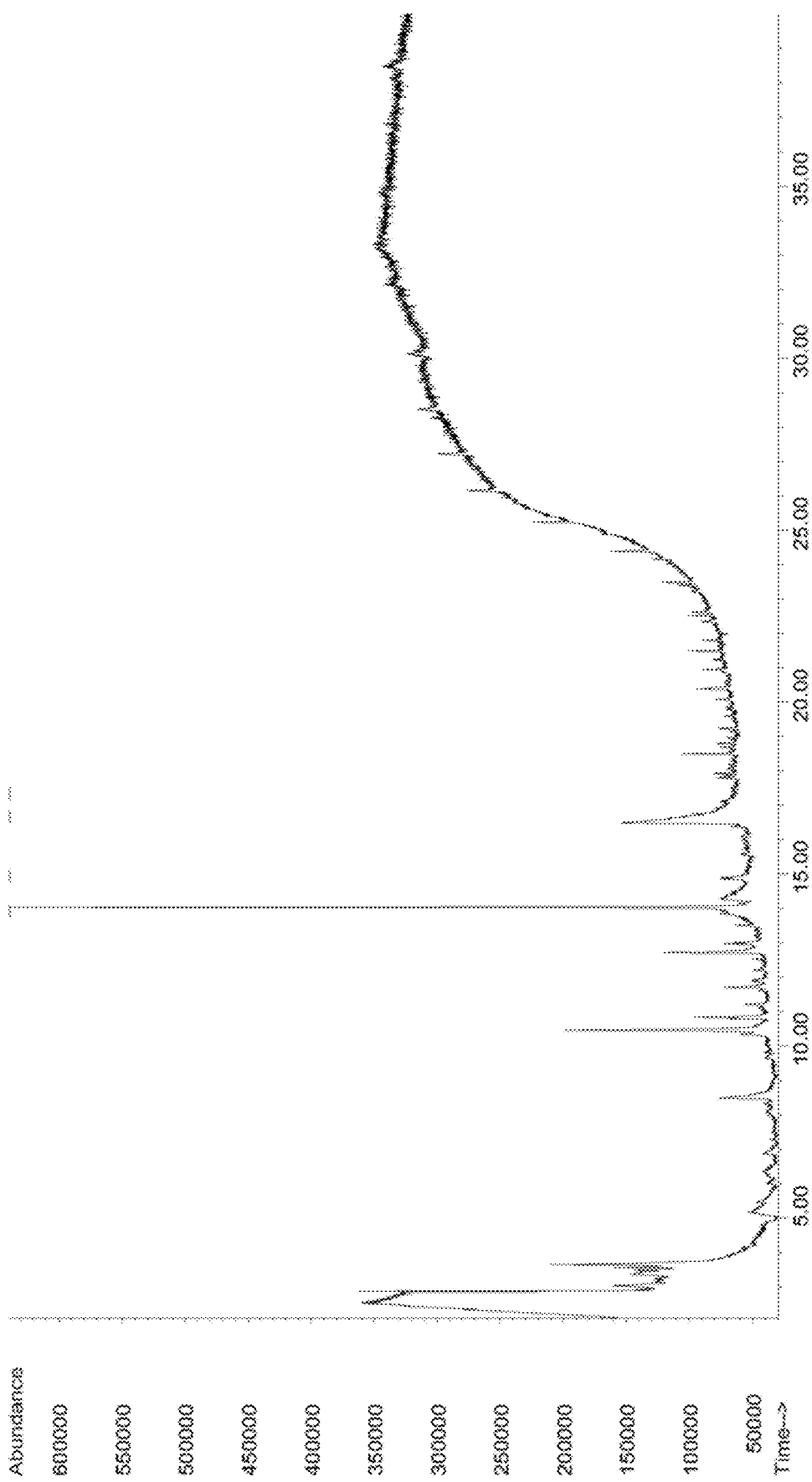
FIG. 8 is a GC/MS chromatogram of plant extract fraction #7 from L_C18_40% HPLC fractions.
Figures 9A, 9B:
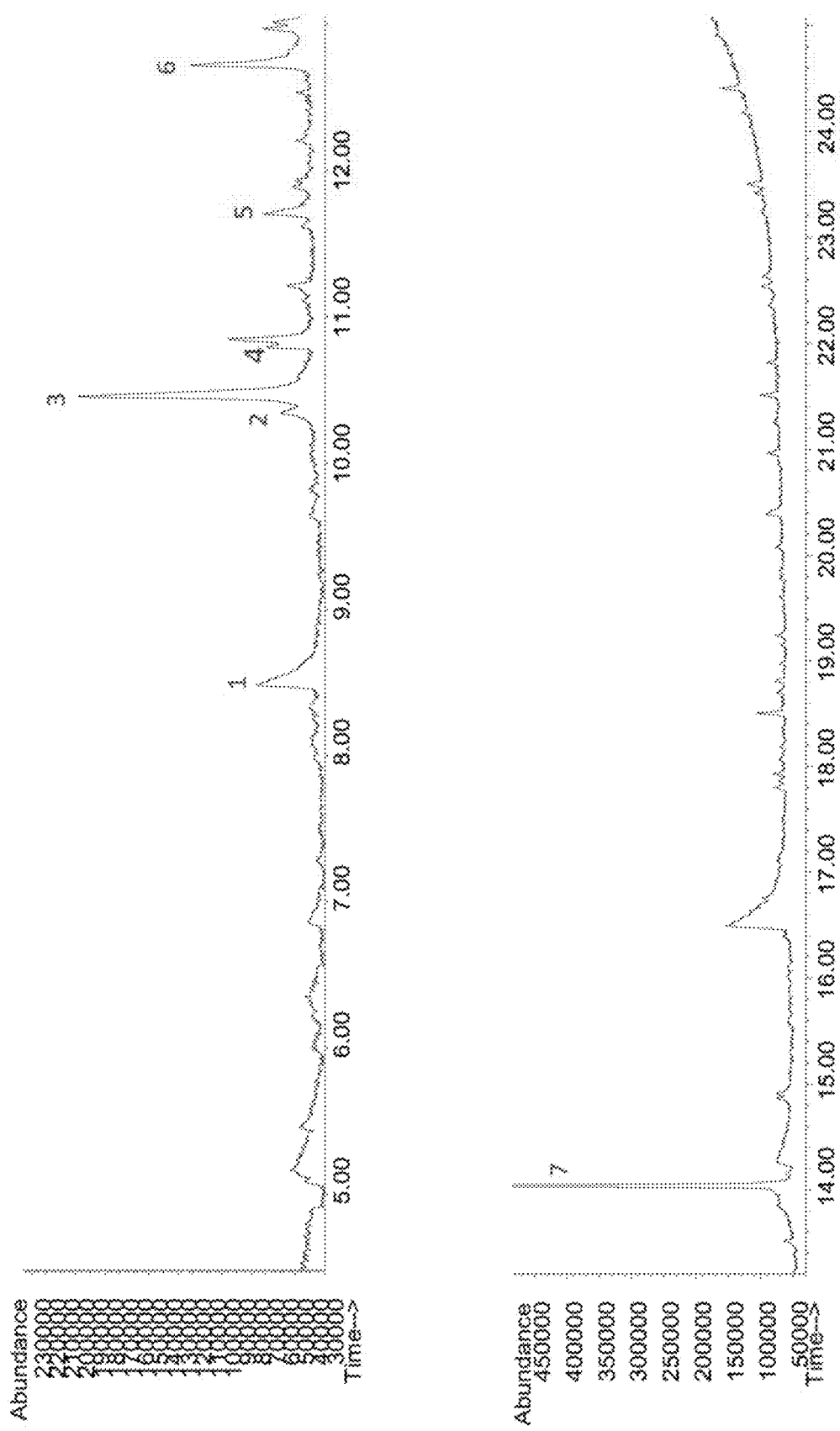
FIGS. 9A and 9B are two graphs showing respective regions of the GC/MS chromatogram of FIG. 8, on an enlarged time scale.
Figure 10:
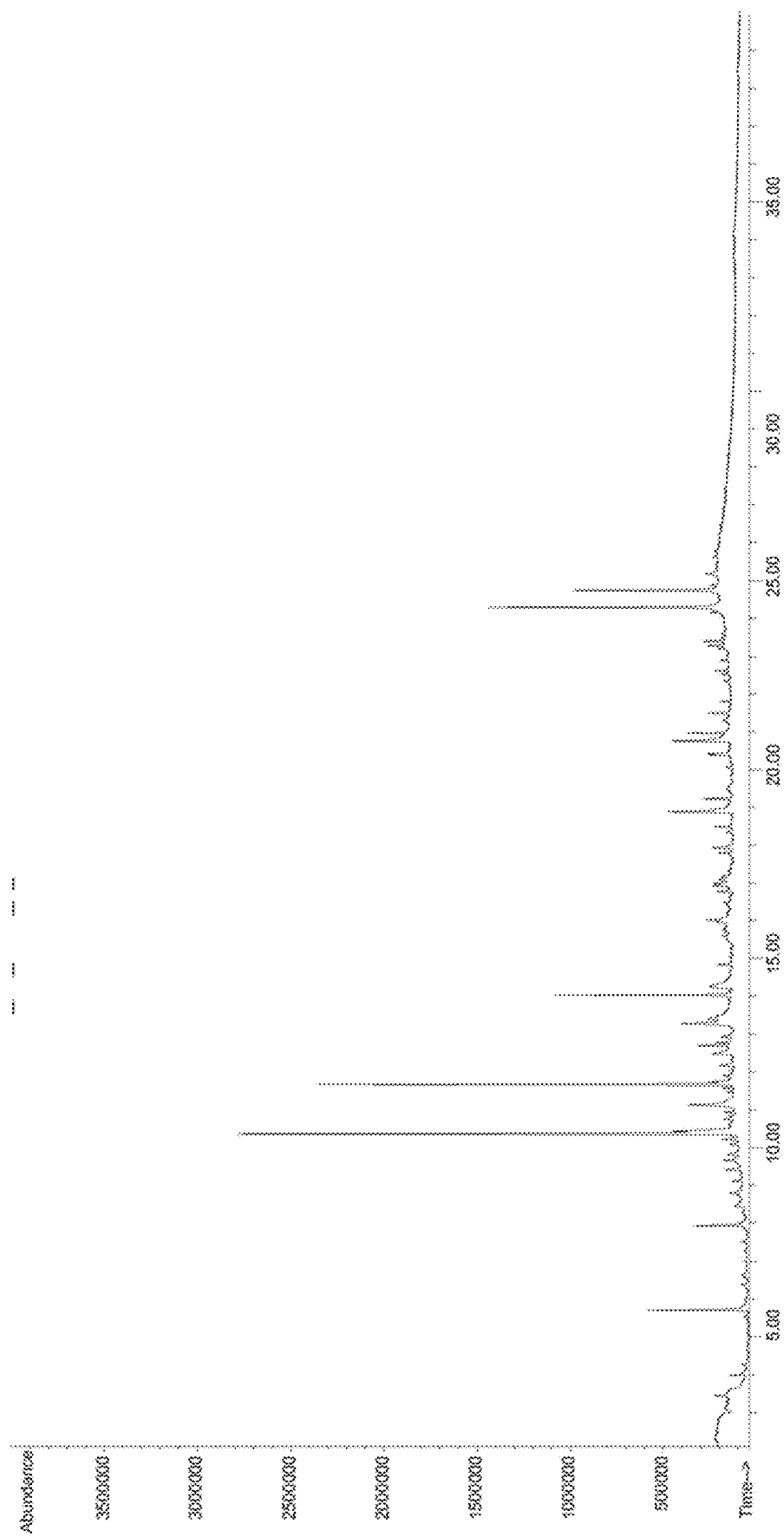
FIG. 10 is a GC/MS chromatogram of plant extract fraction #2 from L_CN-E_EA % HPLC fractions.
Figures 11A, 11B, 11C:
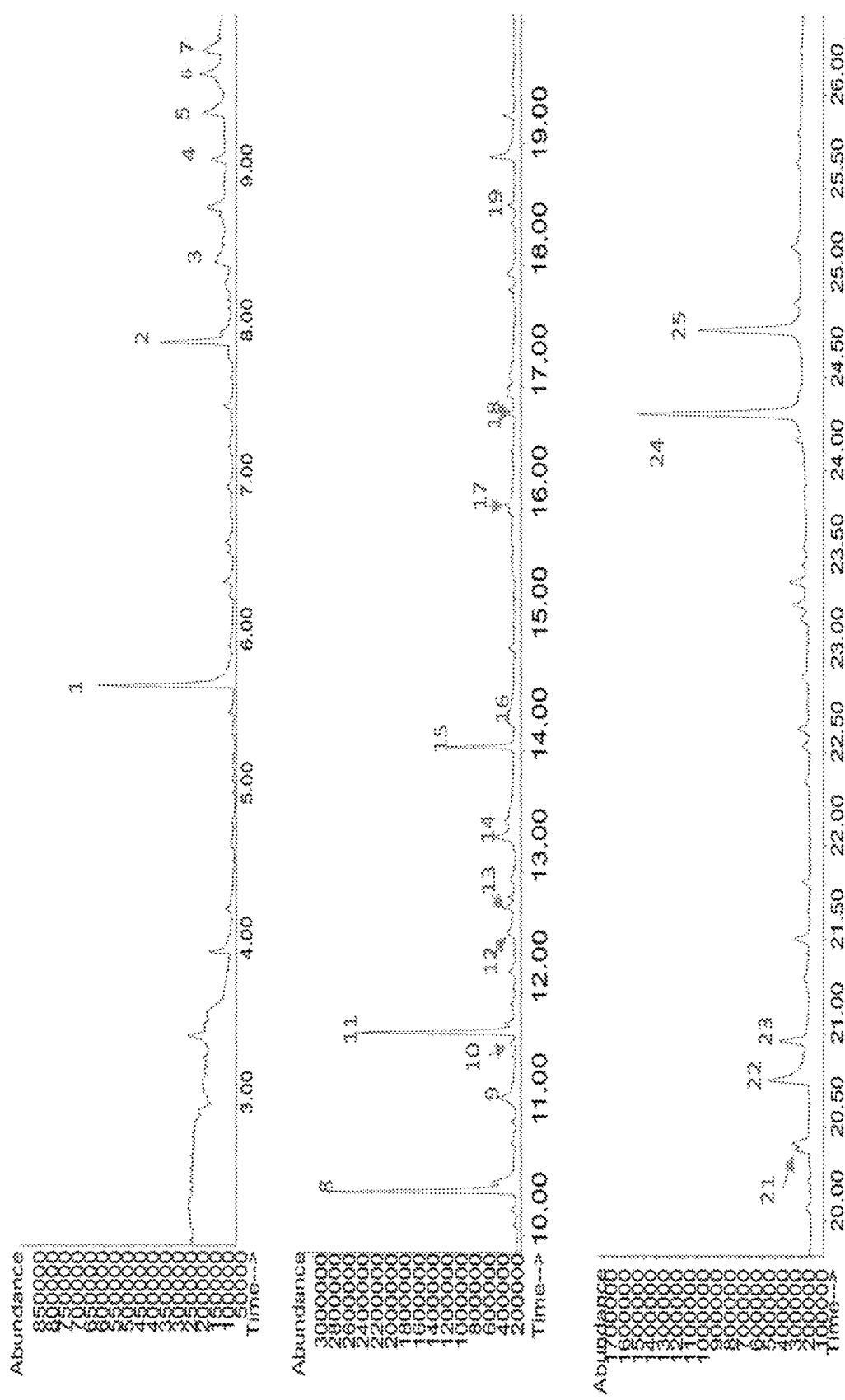
FIGS. 11A-11C are three graphs showing respective regions of the GC/MS chromatogram of FIG. 10, on an enlarged time scale.

*Avicennia Marina* leaves were collected from Saudi Arabia, Thuwal area, Red Sea (22.314278, 39.091701) (FIGS. 5A-5C).

The plants were homogenized using a sterile mortal and pestle with the aid of liquid nitrogen. A DNeasy Plant Mini Kit (QIAGEN) was used to extract the DNA following manufacturer's instructions. DNA amplification was done using multiplex PCR Kit (QIAGEN). Two primers were used rbcL-1F (5'-ATGTCACCACAAACAGAAAC-3'), rbcL-724R (5'-TCGCATGTACCTGCAGTAGC-3') for amplification Ribulose-1,5-bisphosphate carboxylase/oxygenase, (RuBisCO) in the chloroplast DNA. QIAquick PCR purification kit (QIAGEN) was used for PCR products purification. Chain termination (Sanger sequencing) method was applied for sequencing using ABI3730X DNA analyzer. Raw sequences were processed on the software Scanner-2 (Applied Biosystems), which was utilized to assessed sequence quality and trimming. Nearest related and labeled sequences were searched using BLAST against the NCBI nr database.

Sample Extraction and Fractionation

Plants were rinsed thoroughly with sterile seawater and frozen in liquid nitrogen. The plants were extracted with 10% in dichloromethane/methanol (1:1) overnight at room temperature. Then, samples were centrifuged at 13,000 g for 30 min to remove particulate material. Extracts were fractionated using solid phase extraction (SPE) with Bond Elut $C_2$, PPL, $C_{18}$, CN-E columns (Agilent Technologies). Columns were conditioned before fractionation with 1 ml methanol, 5 ml CHROMASOLVE water, and 1 ml acidified CHROMASOLVE water (pH 2). 3 ml of extract was loaded onto the column, and eluted with 500 μl of a gradually non-polar 10-100% water/methanol gradient (10% step size). 10 resin extracts were lost through the extraction process. Fractions were dried in a vacuum (CentriVap Complete, Labconco, Kansas City, Montana, USA).

HIV-1 RT Assay

HIV-1 RT reverse transcriptase activities were analyzed with an EnzChek Reverse Transcriptase Assay Kit (Molecular Probes, Life Technologies) according to the manufacturer's instructions. The PicoGreen reagent provided with the kit was added and the resulting RNA DNA duplexes were determined using a spectrofluorometer SpectraMax reader (Molecular Devices) using the 480/520 nm filter set.

33.4 High-Performance Liquid Chromatography (HPLC)

The HPLC fractionation was analyzed using Agilent Technologies 1260 infinity. The sample was injected with 250 μl of material (approximately 250 mg of dry weight) with a flow rate of 1 ml/min using ZOR BEX RX-C8, 9.4 mm, 250 mm column (Agilent Technologies), with 50% water and 50/methanol percentage. UV spectra were developed in the 210-450 nm wavelength range and the resulting chromatograms were integrated at different wavelengths in function of the UV absorption maxima of each component.

Gas Chromatography and Mass Spectroscopy (GC-MS)

The Gas chromatography-Mass spectrometry (GC-MS) analysis of the bioactive plant extracts was preformed using Agilent 7890A gas chromatography system coupled to an Agilent MS model 5975C with triple axis detector (Agilent Technologies). The GC-MS was equipped using 30 m×250 m; film thickness: 0.25 m HP-5MS capillary column (Agilent Technologies) with split ratio 10:1. Oven temperature was 50 C.° for 1 min to 300 C.° for 35 min under a constant helium pressure (10 psi). 1 μl of respective diluted samples was automatically injected.

Cell Culture

HeLa cells were kept under standard conditions at 37° C. in 5% $CO_2$ in Dulbecco's modified Eagle medium (DMEM containing GlutaMAX-1; 4.5 g/L D-Glucose; Pyruvate; Gibco, Darmstadt, Germany) supplemented with 10% fetal bovine serum (Life Technologies) and 1% antibiotic-antimycotic solution (Life Technologies).

High-Content Screening and Analysis.

HeLa cells were transferred into 384-well plates, seeded at a density of 2000 cells per well and incubated for 24 h in 25 μl of Dulbecco's modified Eagle's medium (DMEM containing GlutaMAX-1; 4.5 g/L D-Glucose; Pyruvate; Gibco, Darmstadt, Germany). The HCS allows the elimination of not living or heavily damaged cells from analysis. Therefore, the analysis done using high content machine focused on the living HeLa cells in the culture and is not due to cell damage. Followed by subjected to four different panels to satin 10 cellular targets[13]. Staining was done using different set of panels in order to avoid the overlap between the fluorescent channels. For each extracted sample was repeated four times and data set results were normalized to untreated controls to score between −1 and 1. Control wells were untreated (without fractions). In all cases unless otherwise indicated, cells were fixed with 4% formaldehyde for 20 min. Then were subjected to permeabilization, blocking, and washing steps by using HCS-optimized reagents such as Wash Buffer (WB), Wash Buffer II (WBII), Blocking Buffer (BB) and Permeabilization Buffer (PB) (Thermo Fisher Scientific). Eventually, all plates were washed three times with WB and stored at 4° C. until further analysis. Panels are: (1) Fixed cells were permeabilized for 17 min, washed twice with WB, then blocked for 30 min. Followed, stained by p53 antibody (MA512557-Thermo Scientific) and Cleaved Caspase-9 antibody (ASP315-Thermo Scientific) both antibodies were prepared on blocking buffer for 1 h. The secondary staining solution was added 1:500 GAR-DyLight 488 and 1:500 GAM-DyLight 550 (Thermo Fischer Scientific) in WB for 1 h. Afterward, cells were washed once with WBII and stained with Hoechst33342 (OG1726671-Thermo Scientific) for 10 min. (2) Cells were incubated with ER (ER-Tracker Blue-White DPX, Life Technologies) and Lyso (LysoTracker Red DND-99, Life Technologies) under normal cell culture conditions. After fixation, cells were washed twice with WB and incubated with Wheat Germ Agglutinin, Alexa Fluor 488 Conjugate (Life Technologies) for 10 min. Then nucleus was stained with Hoechst Stain (OG1726671-Thermo Scientific) for 10 min. (3) After fixing the cells, cells permeabilized for 15 min and blocked for 15 min. Followed by staining solution Phalloidin-FLTC (Sigma-Aldrich), Beta-3 Tubulin Antibody (MA1-19187, Thermo Fischer Scientific) for 1 h. Then cells were washed twice with BB and stained by 1:500 GAM-DyLight 550 (Thermo Fischer Scientific) in BB for 1 h. Then nucleus was stained with Hoechst Stain (OG1726671-Thermo Scientific) for 10 min. (4) Cells were incubated with mitochondrial dye (MitoTracker Orange CMTMRos, M7510, Life technologies) under normal cell culture conditions for 30 min. Then, stained by NFkappaB/p65 Antibody (PA5-16545) and Cytochrome C Antibody (MA5-11823-Thermo Scientific) for 1 h. After, cells were incubated with WBII for 15 min and washed twice with WB. Then, secondary staining solution was added 1:500 GAR-DyLight 550 (Thermo Fischer Scientific) in WB for 1 h. Next, cells were incubated with WBII for 10 min and stained with a solution of Hoechst33342 (OG1726671-Thermo Scientific) for 10 min[13].

XTT-Microculture Tetrazolium Assay

Cells were growing, counted, and inoculated into 96-well microtiter plates at density of 2000 cells. After 24 h, fractions are added with 25 µg/ml concentration to triplicate culture wells, and cultures were incubated for 24 h. Cytotoxicity was measured by XTT colorimetric assay [14]. XTT was diluted 1:10 in RPMI medium and treat cells with 50 µl per microculture wells. The absorbance values of the treatments are read using a spectrophotometer (Molecular Devices Multi-Mode Detection Platform and Software) at the wavelength of 490 nm using the reference absorbance of 650 nm.

Cell Cycle Analysis

HeLa cells were plated in 384-wells. Cells were treated with 25 µg/ml concentration of SPE extract for 24 h under culturing conditions. Cells were fixed with 3.7% formaldehyde for 15 min, washed twice with DPBS and stained with Hoechst 33342 (OG1726671-Thermo Scientific) for 10 min in dark at room temperature. Hoechst dye was prepared in DPBS (mg/ml). Staining with Hoechst 33342 was measured using the Cellomics ArrayScan™ VTI High Content Analysis reader (Thermo Fisher Scientific) and BGRFR 386-23 filter set.

The Cellomics® cell cycle BioApplication automatically classifies each cell's nuclear total intensity into one of cell cycle phase's. Cells classifies as having DNA~2N, 2N<DNA<4N, and DNA~4N are assigned the cell cycle phases G0/G1, S, and G2/M correspondingly. The DNA<2N assigned to damaged or apoptotic cells (Low nuclear intensity value).

Data Analysis

All the experiments were repeated four times and results were normalized to untreated controls. Entirely row data analyses were performed using Graphpad Prism version 6 (GraphPad Software, La Jolla, Calif.). Data are illustrative of at least four replicates. Data are mean t SD. Statistical significance of comparison between two groups was determined by two-tailed Student's t-test where specified. Significant alterations were measured at p-values of less than 0.05.

Results

HIV-1 Reverse Transcriptase Activity

We used a commercially available EnzChek Reverse Transcriptase Assay Kit to examine the possible activity of the fractions. The fractions were tested for potential activity at 1.56 µg/ml concentration, which was used as a cut-off value to determine if the fractions were active or not. Of a total of 20 fractions, 4 extract fractions were demonstrated to reduce RT-HIV-1 activity (FIG. 1A). Hit extracts were re-tested in a dose-dependent manner, with the use of serial dilutions (FIG. 1B). $L\_C_{18}\_80\%$ and L_CN-E_EA fractions showed a strong inhibitory effect starting from 1.56 µg/ml concentration.

Bioactivity of different HPLC fractionations on HIV-1 RT

Figure 2A:
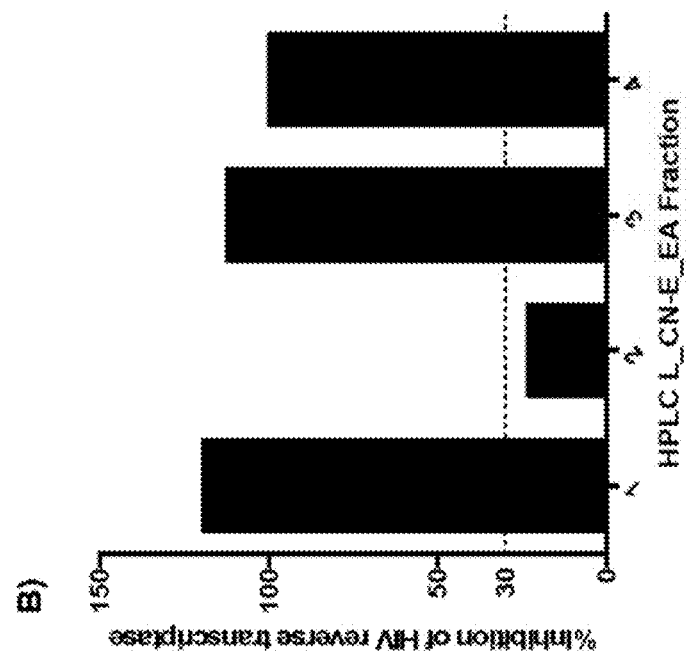
FIGS. 2A and 3B are charts or graphs pertaining to the cytological profiling of *A. marina* leaves.
Figure 2B:
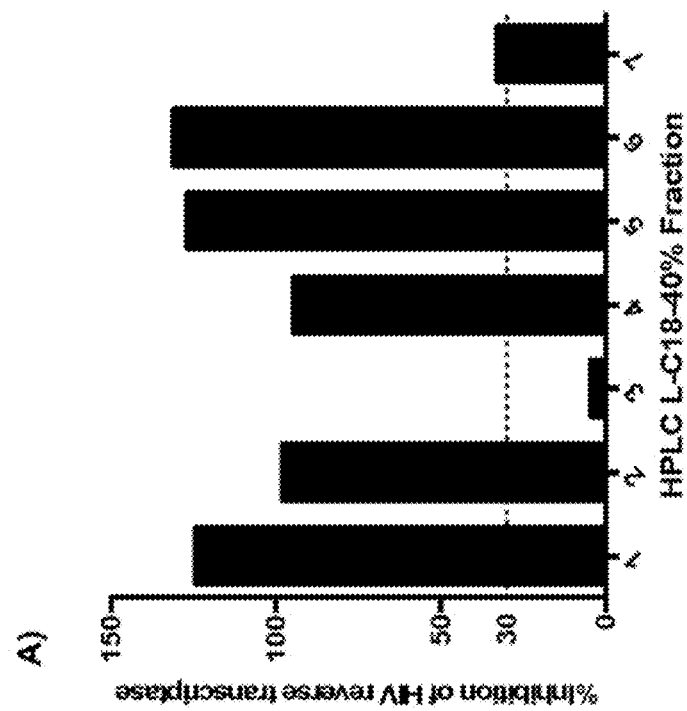

In an effort to isolate the compound in the active fraction that shows the potent inhibitory effect, we investigate $L\_C_{18}\_40\%$ and L_CN-E_EA % extract using HPLC fractionation column to reduce the complexity of the fraction. Moreover, HPLC fractions were tested against HIV-1 RT biochemical assay in 1.56 µg/m concentration. In $L\_C_{18}\_40\%$, fraction 3 and 7 shows a potent inhibitory effect on the RT-HIV-1 assay (FIG. 2A) and in L_CN-E_EA %, fraction 2 shows a potent inhibitory effect on RT-HIV-1 assay (FIG. 2B).

Chemical Analysis of the Active HPLC Fractions

To evaluate possible active chemical compounds that inhibit the activity of HIV-1 RT from *A. marine*, we used GC-MS analysis to identify chemical compounds to $L\_C_{18}\_40\%$ HPLC fractions 3 and 7 as the highest probable candidates inhibitors for anti-HIV-1 compounds. The GC/MS chromatograms for two samples are depicted in (FIGS. 6, 7A-7C, 8, and 9A-98). The compound identified in fraction 3 and 7 are listed in Tables 1 and 2. Fraction #3 was found to contain the higher intensity of the compounds detected compared to Fraction #7. Overlay of GC-MS characterized compounds for HPLC fractions shows common four known chemical compounds. The four compounds are 2-methoxyphenol ($C_7H_8O_2$, 124.137 g/mol), Methyl m-methylbenzoate (C9H10O2, 150.1745 g/mol), isomer of Methyl cinnamate ($C_{10}H_{10}O_2$, 162.185 g/mol) and 2,4-di-t-Butylphenol ($C_{14}H_{22}O$, 206.324 g/mol).

TABLE 1

List of compounds detected in fraction # 3 from L_C18_40% HPLC fractions. Each compound is corresponds to peak # and retention time in minutes. Software AMDIS and library data NIST 11 is used to de-convolute and identify these compounds detected.

| Peak# | Retention Time (min) | Compound ID |
|---|---|---|
| 1 | 3.850 | 1-hydroxy-2-propanone |
| 2 | 6.520 | 2-methyl-3-butene-2-ol |
| 3 | 6.900 | Phenol |
| 4 | 7.590 | 1-butanol-3-methoxy acetate |
| 5 | 8.000 | 2,5-dimethyl-2,5-hexanediol |
| 6 | 8.070 | 3-(1-methylethyl)-2,4-pentanediol |
| 7 | 8.490 | 2-methoxyphenol |
| 8 | 8.855 | Tetrahydro-4-methyl-2H-pyran-2-one |
| 9 | 9.427 | α-methylbenzeneacetaldehyde |
| 10 | 9.679 | 2-(2-ethoxyethoxy)-ethanol acetate |
| 11 | 9.811 | 2-methylbenzofuran |
| 12 | 10.32 | Methyl m-methylbenzoate |
| 13 | 10.385 | Dihydrobenzofuran (Coumaran) |
| 14 | 10.762 | Methyl phenethyl ketone |
| 15 | 11.227 | p-Methylbenzoic acid |
| 16 | 11.317 | Caprolactam |
| 17 | 11.584 | Isomer of Methyl Cinnamate |
| 18 | 11.685 | 4-Hydroxy-3-methoxystyrene |
| 19 | 12.181 | 2,6-Dimethoxyphenol |
| 20 | 12.505 | Isomer of cinnamic acid |
| 21 | 12.704 | Isomer of Methyl cinnamate |
| 22 | 12.929 | Vanillin |
| 23 | 13.297 | Isomer of cinnamic acid |
| 24 | 14.03 | 2,4-di-t-Butylphenol |
| 25 | 14.833 | 3',5'-Dimethoxyacetophenone |
| 26 | 16.019 | 3,5-Dimethoxy-4-hydroxybenzaldehyde |
| 27 | 16.767 | Ethyl m-methylbenzoate |
| 28 | 16.988 | 1-methyl-2-oxocyclohexanecarboxylic acid, methyl ester |
| 29 | 17.312 | Tris(2-chloroisopropyl)phosphate |
| 30 | 17.412 | 6-Hydroxy-4,4,7a-trimethyl-5,6,7,7a-tetrahydrobenzofuran-2(4H)-one |
| 31 | 18.342 | Possibly, Glutaric acid, hept-2-yl non-5-yn-3-yl ester |
| 32 | 18.489 | Hexadecanoic acid, methyl ester |
| 33 | 18.888 | n-Hexadecanoic acid |
| 34 | 20.193 | Methyl p-benzoyl benzoate |
| 35 | 20.371 | Octadecanoic acid, methyl ester |
| 36 | 20.472 | Octadecanoic acid |
| 37 | 21.242 | p,p'-isopropylidenebisphenol |
| 38 | 23.195 | Triethylene glycol di(2-ethylhexoate) |
| 39 | 23.958 | 5,7-Dihydroxyflavanone |
| 40 | 25.734 | 9-Octadecenamide |

TABLE 2

List of compounds detected in fraction # 7 from L_C18_40% HPLC fractions. Each compound is corresponds to peak # and retention time in minutes. Software AMDIS and library data NIST 11 is used to de-convolute and identify these compounds detected.

| Peak# | Retention Time (min) | Compound ID |
|---|---|---|
| 1 | 8.484 | 2-methoxyphenol |
| 2 | 10.344 | Methyl methybenzoate |
| 3 | 10.459 | 2,5-dimethylbenzaldhyde |
| 4 | 10.799 | Methenamine (aminoform) |
| 5 | 11.71 | 2-hydroxy-5-methylacetophone |
| 6 | 12.723 | Isomer of methyl cinnamate |
| 7 | 14.03 | 2,4-di-t-Butylphenol |

In an effort to identify chemical compounds in L-CN-E_EA % HPLC fractions #2 as the highest probable candidates inhibitors for anti-HIV-1 compounds. Further analysis using GC-MS show similar profile to both previous fractions (FIGS. 10 and 11A-11C). The compounds detected by GC-MS include phenol derivative compounds as well as an isomer of Methyl cinnamate ($C_{10}H_{10}O_2$, 162.185 g/mol) and dihydrobenzofuran (Coumaran) ($C_8H_8O$ 120.14852 g/mol) are listed in Table 3

TABLE 3

List of compounds detected in fraction # 2 from L-CN-E_EA % HPLC fractions. Each compound is corresponds to peak # and retention time in minutes. Software AMDIS and library data NIST 11 is used to de-convolute and identify these compounds detected.

| Peak # | Retention Time (min) | Compound ID |
|---|---|---|
| 1 | 5.712 | Possibly 1-methylbutane-1,3-diol |
| 2 | 7.936 | 2,5-dimethyl-2,5-hexanediol |
| 3 | 8.456 | 2-methoxyphenol |
| 4 | 9.112 | 5-Isopropyl-1,4-dimethyl-1-cyclopentene |
| 5 | 9.416 | α-methylbenzeneacetaldehyde |
| 6 | 9.671 | 2-(2-ethoxyethoxy)-ethanol acetate |
| 7 | 9.817 | 2-methylbenzofuran |
| 8 | 10.369 | Dihydrobenzofuran (Coumaran) |
| 9 | 11.227 | p-Methylbenzoic acid |
| 10 | 11.584 | Isomer of methyl cinnamate |
| 11 | 11.685 | 4-hydroxy-3-methoxystyrene |
| 12 | 12.499 | Isomer of cinnamic acid |
| 13 | 12.711 | Isomer of methyl cinnamate |
| 14 | 13.297 | Isomer of cinnamic acid |
| 15 | 14.03 | 2,4-di-t-Butylphenol |
| 16 | 14.263 | Possibly 1,6-anhydroglycopyranose |
| 17 | 16.027 | 3,5-Dimethoxy-4-hydroxybenzaldehyde |
| 18 | 16.767 | Ethyl m-methylbenzoate |
| 19 | 18.497 | n-Hexadecanoic acid, methyl ester |
| 20 | 18.901 | n-Hexadecanoic acid |
| 21 | 20.383 | Octadecanoic acid, methy ester |
| 22 | 20.749 | Octadecanoic acid |
| 23 | 20.961 | n-octadecyl isocyanate |
| 24 | 23.958 | Unknown (intense peak) |
| 25 | 24.303 | Unknown (intense peak) |

Cytological Profiling for *A. marina* Using High-Content Core Features

Figures 3A, 3B:
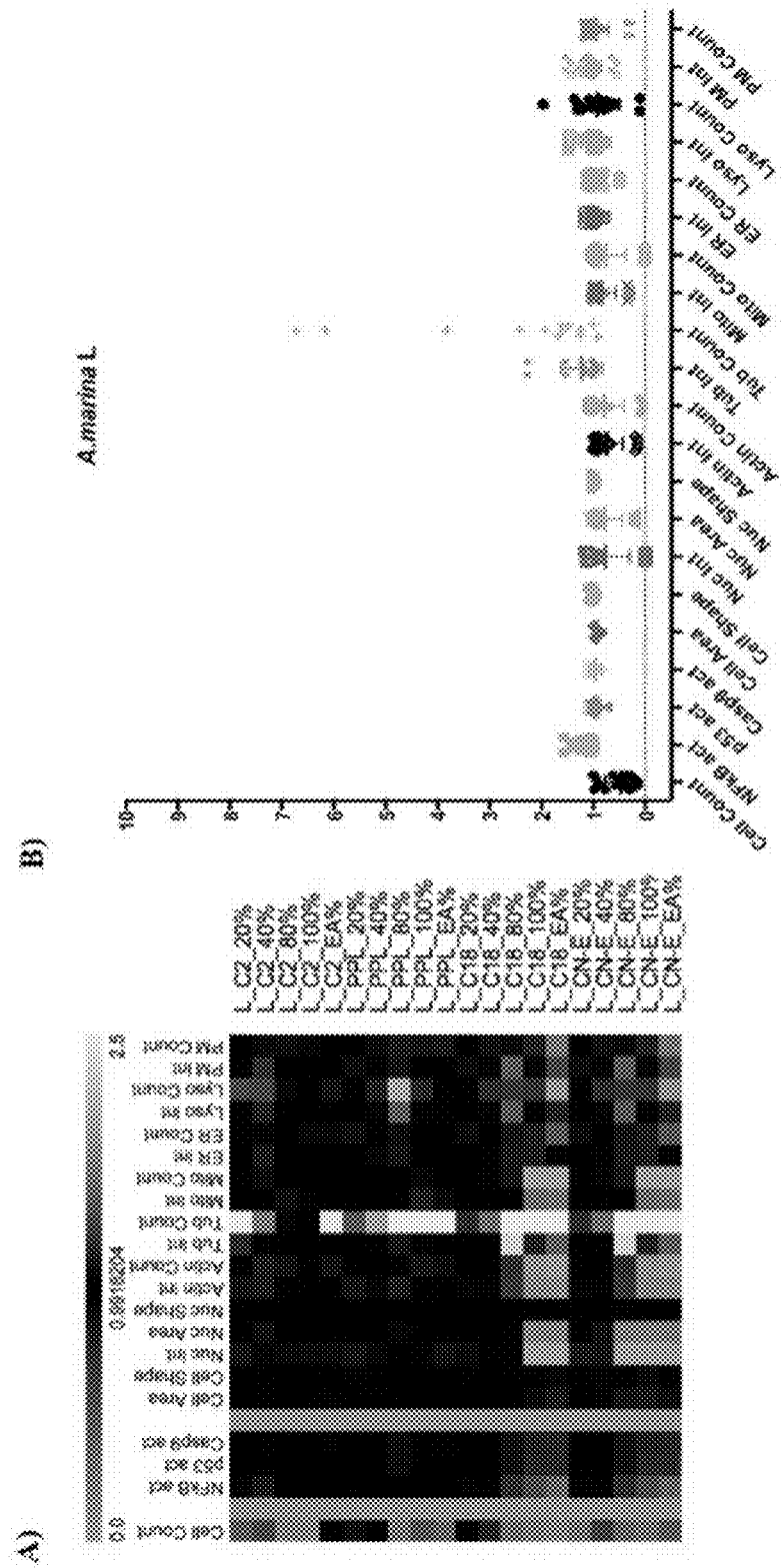
FIG. 3A is a heat map showing cytological profiling dendrogram for *A. marina* leaves.

In order to get more comprehensive information into the whole population of fractions, 21 cellular core features were selected for 12 different cellular markers (FIGS. 3A, 3B) [13]. Our cytological profiling platform core features were generated for *A. marina* leaves. For *A. marina* leaves, extract from higher non-polar gradient looks more effective on the cell count number. Total fractions show no or only weak effects on the whole panel of cellular markers. However, overall fractions show a strong positive effect on tubulin count feature excluding fractions from $C_1a$ and CN-E with higher non-polar concentration. They show high negative effects on nuclear shape and intensity, Actin intensity and count, Mitochondria intensity and count, ER and lysosome count and membrane permeability cell intensity and count.

Figure 4A:
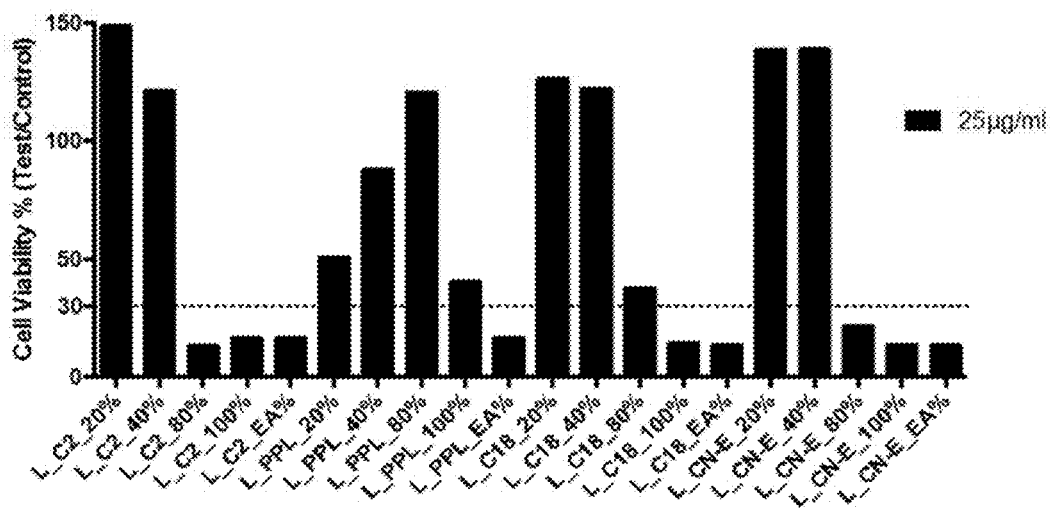
FIG. 4A shows the effect of SPE fractions on cell viability.

Evaluate the viability and cell cycle effect of the SPE fractions Effects of *A. marina* SPE fractions on HeLa cells were evaluated by XTT assay, which measures cell viability (FIG. 4A). Effects of SPE fractions eluted from higher methanol and ethyl acetate concentration shows a strong cytotoxic effect on cell viability.

Figure 4B:
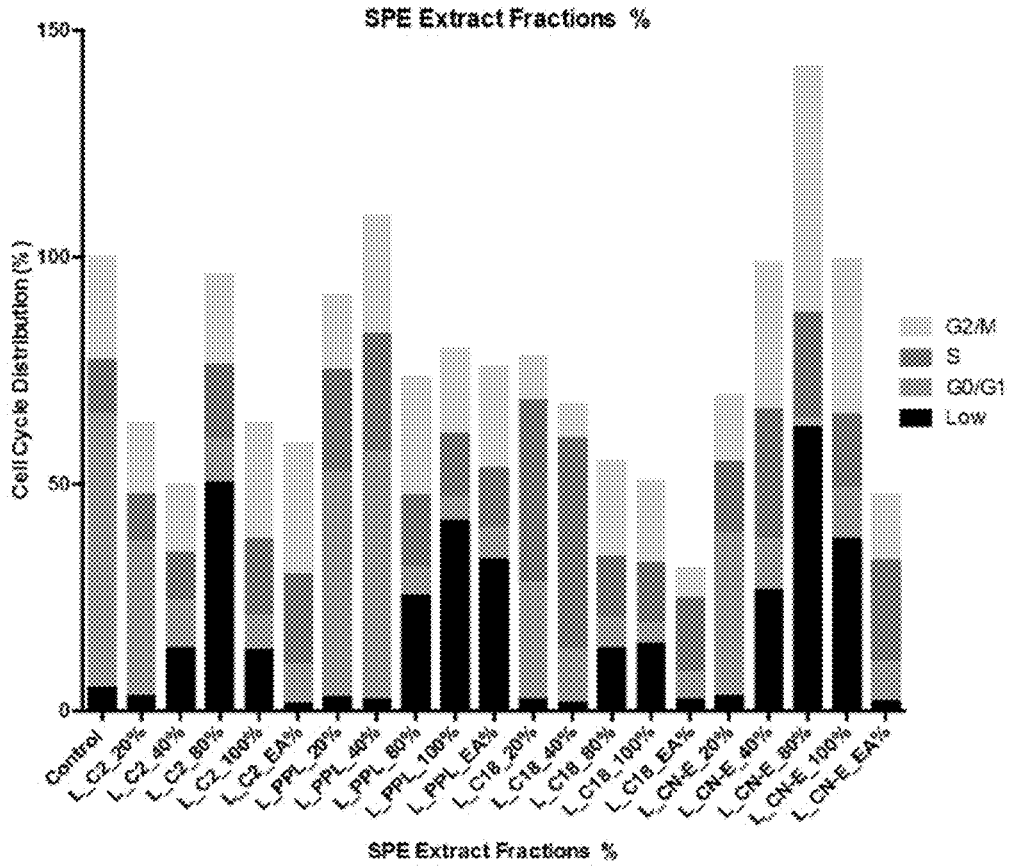

Furthermore, cell cycle analysis was done using high content screening technique. In general, the effect of SPE extract on HeLa cells shows increased in Sub-G1 phase as well as arrest in G0/G1 cell cycle phase (FIG. 4B).

Discussion

Extracts from *Acivennia marina* Leaves as a Source for Novel Anti-HIV-1 Compounds This study demonstrates the bioactivity of *Acivennia marina* leaves as anti-HIV-1. Our results suggest the activity of *A. marina* leaves inhibits the HIV reverse transcriptase enzyme. *A. marina* (grey mangrove), found on the northern coastline of the Red Sea, has been shown to produce several groups of secondary metabolites with anti-HIV activity. These compounds include alkaloids, polyphenols, flavonoids, sulphated polysaccharides, coumarines and triterpenes [15-17]. As our goal was to target "drug-like" compounds, organic solvents were used to extract secondary compounds from *A. marina*, which were subsequently fractioned with high-absorbent capacity for non-polar compounds. Due to the great compositional complexity of natural products such as plants, solid phase cartridges were used to separate the countless compound fractions based on their polarity, and hence simplify their complexity. In an effort to detect the inhibitory activity of fraction HIV-1 RT, a commercial biochemical assay was used to detect the inhibitory activity of SPE fractions on HIV-1 reverse transcriptase enzyme (HIV-1 RT). SPE fractions were tested using one concentration to detect the most active fractions, which were re-tested in order to detect the lowest active dose.

Chemical Analysis of the Active Fractions

In this study, GC-MS is applied to determine the chemical composition of *A. marine* L_$C_{18}$_40% extract for fractions 3 and 7 and L-CN-E_EA % extract for fraction 2, with the purpose of detecting the chemical compounds that could be potential anti-HIV-1 RT. The common chemical compounds were evaluated and proposed as a potential anti-HIV-1 RT. Many polyphenols have been proven to act as multi-target anti-HIV agents compounds [18, 19]. Methyl cinnamate is a phenyl propanoid that shows anti-microbial, anti-flatoxin, antifungal, anti-oxidative [20, 21] and other bioactivity effects [22, 23]. Although it has not demonstrated activity against HIV-1 integrase, the effect of methyl cinnamate against HIV-RT has not been studies[24]. Benzofuran compounds found in both extracts showed activity against HIV reverse transcriptase [25]. In this study, methyl cinnamate was present in abundance in HPLC fraction 7, but in a lesser amount in HPLC fraction 3. 2-Methoxy phenol is well-known as gluaiacol which has medicinal effects, relaxing bronchial secretions in the respiratory tract. It has been reported that gluaiacol is efficient in blocking HIV-1 reactivation in cases of virus latency but it has never been reported to show activity against HIV RT [26]. Methyl m-methylbenzoate was detected in low abundance in both HPLC fractions and no bioactivity was reported. Interestingly, 2,4-di-t-butylphenol displayed higher abundance in L_C$_{18}$_40% extract for both fraction 3 and 7. 2,4-di-t-butylphenol has been reported to have strong antibacterial, antioxidant activity, anticancer activity and antifungal activity [27-30]. In L-CN-E_EA % extract for fraction 2, two intense unknown peaks were detected but they could not be recognised. LC-MS and NMR can be used to determine the structure of those peaks.

Study the Effect of *A. marina* Leaves Fraction on Cell-Based Sing High-Content Screening and XTT Assay The high-content imaging cell-based technique was applied in an effort to determine the secondary effects of the compound fractions of *A. marina* leaves. These were stained with a different cellular marker to generate 21 cellular core features corresponding to intensity, shape, and count for both single cells and well averages, and was accomplished as previously explained [7, 8, 13]. Assessment of cellular toxicity of SPE fractions was done by XTT assay, which is an indicator of cell mitochondria metabolism [31, 32]. Most extract fractions showed increasing effect on Sub-G1 as well as an arrest in G0/G1. Previously, a similar effect was reported for extracts of *A. marina* leaves [33]. The anticancer activity of *A. marina* leaf extracts was studied by Huang and co-workers. They reported that these extracts initiated apoptosis and inhibited migration of liver and breast cancer cells [33]. This result supported previous research on the effect of *A. marina* extract against cancer cells [34, 35].

CONCLUSIONS

In conclusion, this study demonstrated for the first time that *A. marina* leaves contain potent anti-HIV-1 RT compounds that constitute promising candidates for the development of new HIV-1 inhibitors. The chemical profile analysis indicated polyphenol compounds that were well-known to possess anti-HIV-1 RT activity and some compounds that need further isolation and testing to validate if they possess activity. In the future, further analyses for the proposed chemical compounds are required to determine the active chemical compound anti-HIV-1 RT. Moreover, *A. marina* leaves should be tested against other viral infections as well.

1. de Béthune, M.-P., *Non-nucleoside reverse transcriptase inhibitors (NNRIs), their discovery development, and use in the treatment of HIV-1 infection: a review of the last 20 years (1989-2009)*. Antiviral research, 2010. 85(1): p. 75-90.
2. Kim, B. S., et al., *Identification of a novel type of small molecule inhibitor against HIV-1*. BMB reports, 2015. 48(2): p. 121.
3. Deeks, S. G. and A. N. Phillips, *Clinical review: HIV infection, antiretroviral treatment, ageing, and non-AIDS related morbidity*. Bmj, 2009. 338: p. 288-292.
4. Kremb, S., et al., *Aqueous extracts of the marine brown alga Lobophora variegata inhibit HIV-1 infection at the level of virus entry into cells*. PloS one, 2014. 9(8): p. e103895.
5. Jung, M., S. Lee, and H. Kim, *Recent studies on natural products as anti-HIV agents*. Current medicinal chemistry, 2000. 7(6): p. 649-661.
6. Lai, M.-T., et al., *In vitro characterization (If MK-1439, a novel HIV-1 nonnucleoside reverse transcriptase inhibitor*. Antimicrobial agents and chemotherapy, 2014. 58(3): p. 1652-1663.
7. Young, D. W., et al., *Integrating high-content screening and ligand-target prediction to identify mechanism of action*. Nature chemical biology, 2008. 4(1): p. 59-68.
8. Schulze, C. J., et al., *"Function-first" lead discovery: mode of action profiling of natural product libraries using image-based screening*. Chemistry & biology, 2013. 20(2): p. 285-295.
9. Korn, K. and E. Krausz, *Cell-based high-content screening of small-molecule libraries*. Current opinion in chemical biology, 2007. 11(5): p. 503-510.
10. Sumiya, E., et al., *Cell-morphology profiling of a natural product library identifies bisebromoamide and miuraenamide A as actin filament stabilizers*. ACS chemical biology, 2011. 6(5): p. 425-431.
11. Shum, D., et al., *High-content assay to identify inhibitors of dengue virus infection*. Assay and drug development technologies, 2010. 8(5): p. 553-570.
12. Giuliano, K. A., et al., *High-content screening: a new approach to easing key bottlenecks in the drug discovery process*. Journal of Biomolecular Screening, 1997. 2(4): p. 249-259.
13. R. Voolstra, S.K.a.C., *High-resolution phenotypic profiling of natural products-induced effects on the single-cell level* Submitted, 2016.
14. Berridge, M. V., et al., *The biochemical and cellular basis of cell proliferation assays that use tetrazolium salts*. Biochemica, 1996. 4(1): p. 14-19.
15. Singh, I. P., S. B. Bharate, and K. Bhutani, *Anti-HIV natural products*. CURRENT SCIENCE-BANGALORE-, 2005. 89(2): p. 269.
16. Yang, J., et al., *A natural theaflavins preparation inhibits HIV-1 infection by targeting the entry step: potential applications for preventing HIV-1 infection*. Fitoterapia, 2012. 83(2): p. 348-355.
17. Behbahani, M., *Evaluation of anti-HIV-1 activity of a new iridoid glycoside isolated from Avicennia marina, in vitro*. International immunopharmacology, 2014. 23(1): p. 262-266.
18. Kim, H. J., et al., *HIV-1 integrase inhibitory phenylpropanoid glycosides from Clerodendron trichotomum*. Archives of pharmacal research, 2001. 24(4): p. 286-291.
19. Andrae-Marobela, K., et al., *Polyphenols: a diverse class of multi-target anti-HIV-1 agents*. Current drug metabolism, 2013. 14(4): p. 392-413.
20. Prakash, B., et al., *Safety assessment of Zanthoxylum alatum Roxb. essential oil, it antifungal, antiaflatoxin, antioxidant activity and efficacy as antimicrobial in preservation of Piper nigrum L. fruits*. International journal of food microbiology, 2012. 153(1): p. 183-191.
21. Huang, Q.-S., et al., *Inhibitory effects of methyl trans-cinnamate on mushroom tyrosinase and its antimicrobial activities*. Journal of agricultural and food chemistry, 2009. 57(6): p. 2565-2569.
22. Lima, F. J., et al., *Antispasmodic and myorelaxant effects of the flavoring agent methyl cinnamate in gut: Potential inhibition of tyrosine kinase*. European journal of pharmacology, 2014. 740: p. 192-199.
23. Vasconcelos-Silva, A. A., et al., *Vasorelaxation induced by methyl cinnamate, the major constituent of the essential oil of Ocimum micranthum, in rat isolated aorta*. Clinical and Experimental Pharmacology and Physiology, 2014. 41(10): p. 755-762.
24. Mazumder, A., et al., *Inhibition of human immunodeficiency virus type-1 integrase by curcumin*. Biochemical pharmacology, 1995. 49(8): p. 1165-1170.
25. James, C. A., et al., *Nucleotide competing reverse transcriptase inhibitors: Discovery of a series of non-basic benzofurano [3, 2-d] pyrimidin-2-one derived inhibitors*. Bioorganic & medicinal chemistry letters, 2013. 23(9): p. 2781-2786.

26. Murry, J. P., et al., *Sulfonation pathway inhibitors block reactivation of latent HIV-1*. Virology, 2014. 471: p. 1-12.
27. Malek, S. N. A., et al., *Cytotoxic components of Pereskia bleo (Kunth) DC. (Cactaceae) leaves*. Molecules, 2009. 14(5): p. 1713-1724.
28. Sani, H. L, et al., *Effects of standardized stem bark extract of Mangifera indica L. in wistar rats with 2, 4-dinitrophenylhydrazine-induced haemolytic anaemia*. Pharmacognosy Journal, 2015. 7(2): p. 89-96.
29. Yoon, M.-A., et al., *Antioxidant effects of quinoline alkaloids and 2, 4-di-tert-butylphenol isolated from Scolopendra subspinipes*. Biological and Pharmaceutical Bulletin, 2006. 29(4): p. 735-739.
30. Dharni, S., et al., *Purification, characterization, and in vitro activity of 2, 4-di-tert-butylphenol from Pseudomonas monteilii PsF84: conformational and molecular docking studies*. Journal of agricultural and food chemistry, 2014. 62(26): p. 6138-6146.
31. Gerlier, D. and N. Thomasset, *Use of MTT colorimetric assay to measure cell activation*. Journal of immunological methods, 1986. 94(1-2): p. 57-63.
32. van Meerloo, J., G. J. Kaspers, and J. Cloos, *Cell sensitivity assays: the MTT assay*. Cancer cell culture: methods and protocols, 2011: p. 237-245.
33. Huang, C., et al., *Polyphenol-rich Avicennia marina leaf extracts induce apoptosis in human breast and liver cancer cells and in a nude mouse xenograft model*. Oncotarget, 2016.
34. Behbahani, M. and H. Sadeghi-aliabadi, *Antiproliferative activity and apoptosis induction of crude extract and fractions of Avicennia marina*. Iranian journal of basic medical sciences, 2013. 16(11): p. 1203-1208.
35. Bhimba, B. V., et al., *Anticancer and antimicrobial activity of mangrove derived fungi Hypocrea Iixii VB1*. Chinese journal of natural medicines, 2012. 10(1): p. 77-80.

The invention claimed is:

1. A composition for inhibiting HIV-1 reverse transcriptase activity comprising an effective amount of an extract of *Avicennia marina*, wherein the extract comprises a C1-C3 alcohol and/or ethyl acetate (EA) and is obtained by a method comprising:
(i) contacting *Avicennia marina* with a first solvent comprising an alcohol and one or more additional solvents to obtain a solution;
(ii) fractionating the solution using solid phase extraction (SPE) with effective amounts of a second solvent comprising a C1-C3 alcohol or ethyl acetate (EA), or combinations thereof, to produce the extract of *Avicennia marina*.

2. The composition of claim 1 wherein the method further comprises fractionating the SPE fraction using high performance liquid chromatography and a solvent comprising aqueous methanol, aqueous ethanol, methanol or ethanol.

3. The composition of claim 1 wherein the second solvent comprises at least about 50% water by volume.

4. The composition of claim 1 wherein the second solvent comprises at least about 50% $C_1$-$C_3$ alcohol by volume.

5. The composition of claim 1 wherein the second solvent comprises at least about 50% methanol by volume.

6. The composition according to claim 1 wherein said extract is in liquid form.

7. The composition according to claim 1 wherein said extract is in semi-liquid form.

8. The composition of claim 1, wherein the extract comprises a compound selected from the group consisting of 2-methoxyphenol, methyl m-methylbenzoate, methyl cinnamate, 2, 4-di-t-butylphenol, and combinations thereof.

9. The composition of claim 1, wherein the *Avicennia marina* is collected from the Red Sea Shore.

10. The composition of claim 1, wherein the *Avicennia marina* is contacted with a solvent comprising dichloromethane/methanol (1:1) in step (i) to produce the solution.

11. The composition of claim 1, wherein the *Avicennia marina* solution is fractionated using SPE with ethyl acetate to produce the SPE fractions.

* * * * *